United States Patent
Gjerde et al.

(10) Patent No.: US 6,355,417 B2
(45) Date of Patent: Mar. 12, 2002

(54) BAND ARRAY DISPLAY OF POLYNUCLEOTIDE SEPARATIONS

(75) Inventors: Douglas T. Gjerde, Saratoga; Paul D. Taylor, Palo Alto, both of CA (US)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/039,061

(22) Filed: Mar. 13, 1998

Related U.S. Application Data

(60) Provisional application No. 60/077,998, filed on Mar. 13, 1998, provisional application No. 60/077,875, filed on Mar. 13, 1998, and provisional application No. 60/041,095, filed on Mar. 14, 1997.

(51) Int. Cl.[7] ............................. C12Q 1/68; C12M 1/34; B01D 15/08; G06F 19/00
(52) U.S. Cl. ............................. 435/6; 435/5; 435/287.2; 210/198.2; 210/635; 210/656; 702/19; 702/20; 702/22
(58) Field of Search ............................. 435/5, 6; 356/72, 356/73; 526/347.2

(56) References Cited

U.S. PATENT DOCUMENTS

| 3,562,501 | A | * | 2/1971 | Mears | 235/150 |
| 4,927,265 | A | | 5/1990 | Brownlee | 356/73 |
| 5,203,992 | A | * | 4/1993 | Brouen | 210/198.2 |
| 5,585,236 | A | | 12/1996 | Bonn et al. | 435/5 |
| 5,614,365 | A | * | 3/1997 | Tabor et al. | 435/6 |
| 5,627,643 | A | * | 5/1997 | Birnbaum et al. | 356/344 |
| 5,666,435 | A | | 9/1997 | Burgi et al. | 382/129 |

FOREIGN PATENT DOCUMENTS

| EP | 0393776 A2 | * 10/1990 |
| WO | WO 99/34205 | 7/1999 |

OTHER PUBLICATIONS

Maniatis et al Molecular Cloning A Laboratory Manual see p. 6.2–6.19, 1989.*
P. R. Haddad and P. E. Jackson "Ion Chromatography"; Elsevier NY: 1990 p. 100.

* cited by examiner

Primary Examiner—Kenneth R. Horlick
Assistant Examiner—Jeffrey Siew
(74) Attorney, Agent, or Firm—William B. Walker

(57) ABSTRACT

A method and apparatus for representing double stranded nucleic acid fragments which have been separated by a chromatographic process as an array of bands which can be accurately quantified, optimized and stored. Using, for example, a Matched Ion Polynucleotide Chromatography (MIPC) process, an analog output from a UV detector is digitized and input to a computer. The digitized signal is converted to a linear array of bands which may be displayed on a video display terminal. The intensity and/or color of a band may correlate to the amount of double stranded nucleic acid in the respective fraction or the respective double stranded nucleic acid fragment above a user selected threshold level at a corresponding point in the digitized signal. The calculated base pair length, concentration, and retention time of each band in the array of bands may be displayed in alphanumeric form.

16 Claims, 14 Drawing Sheets

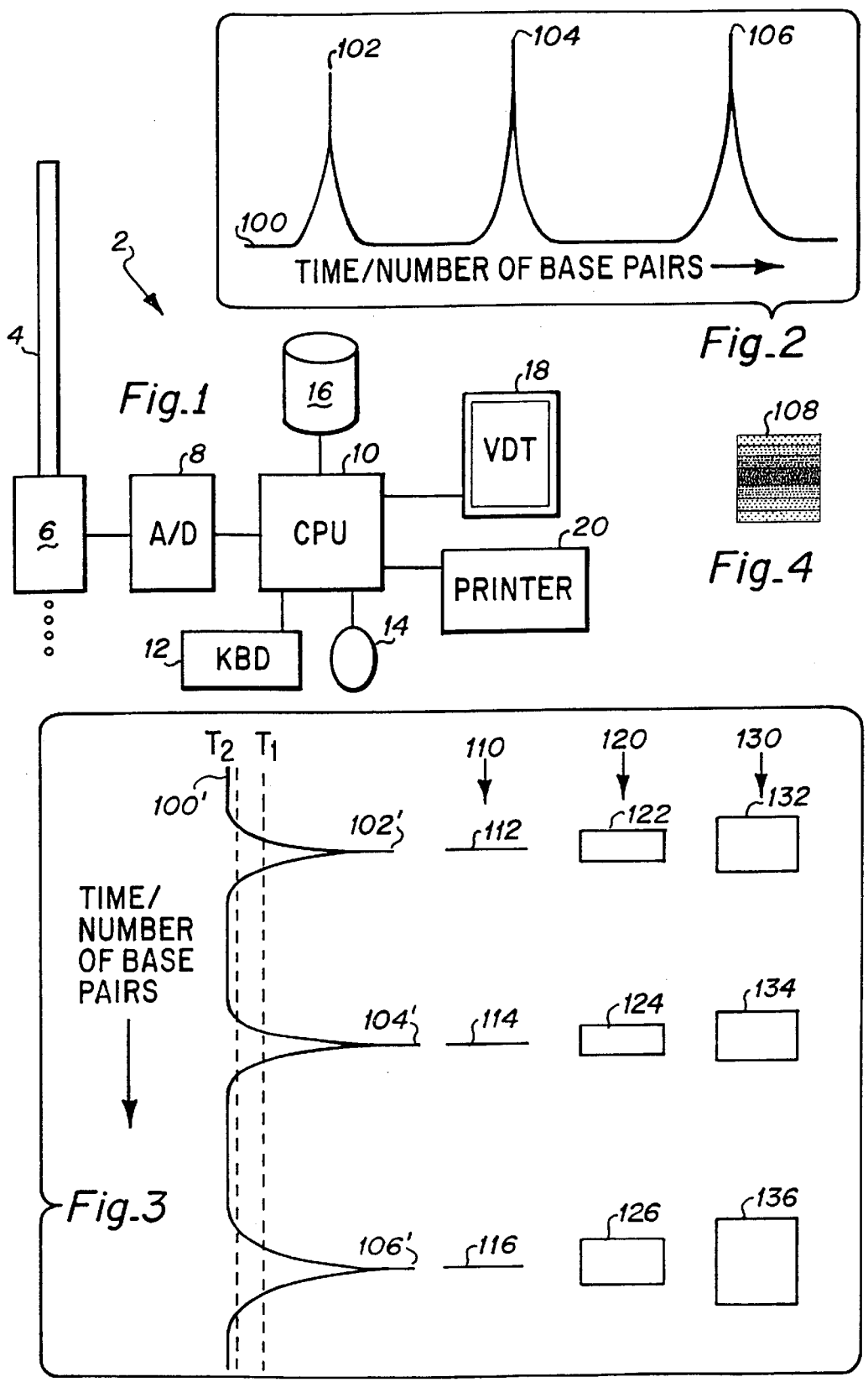

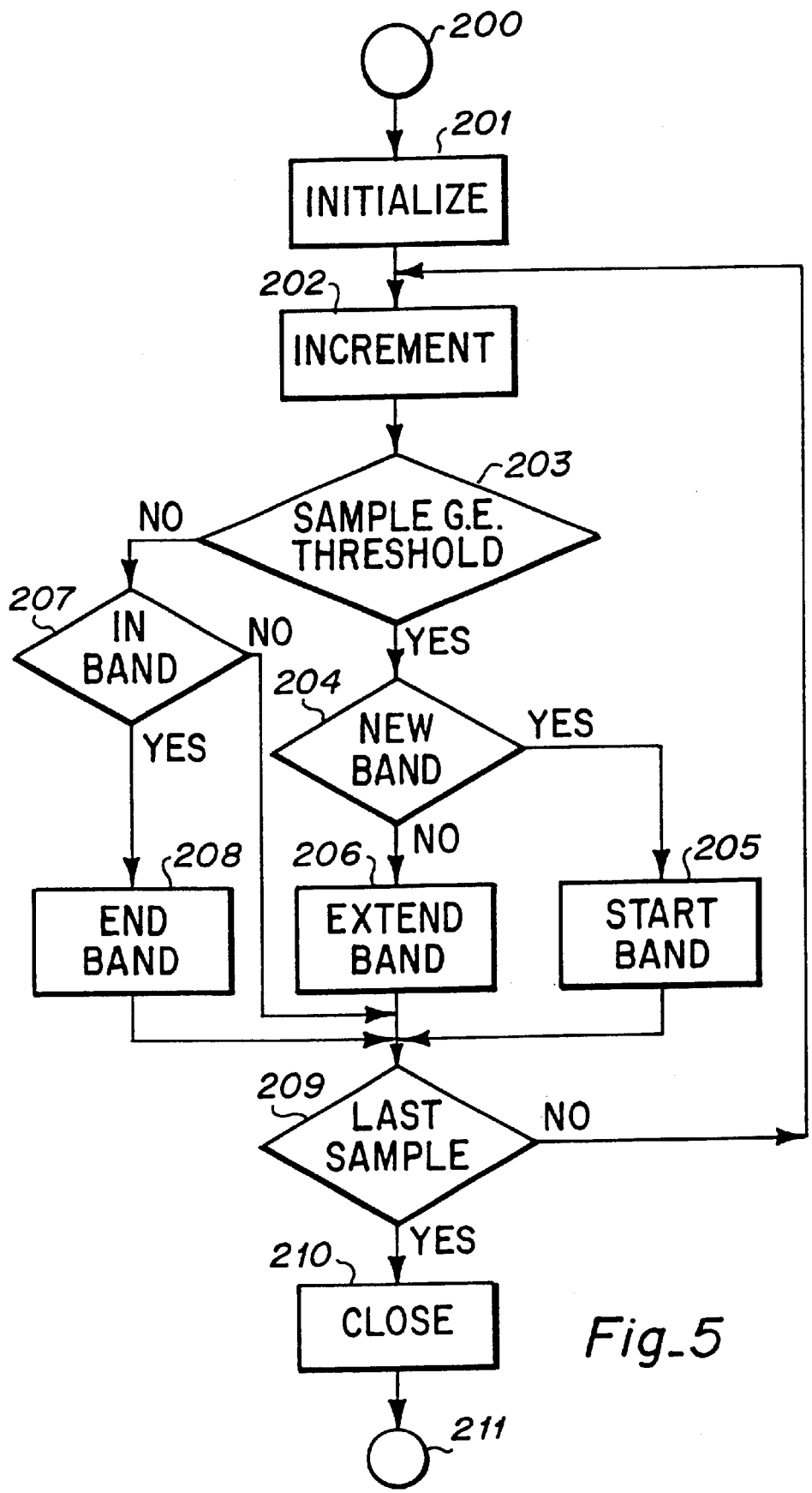
Fig_5

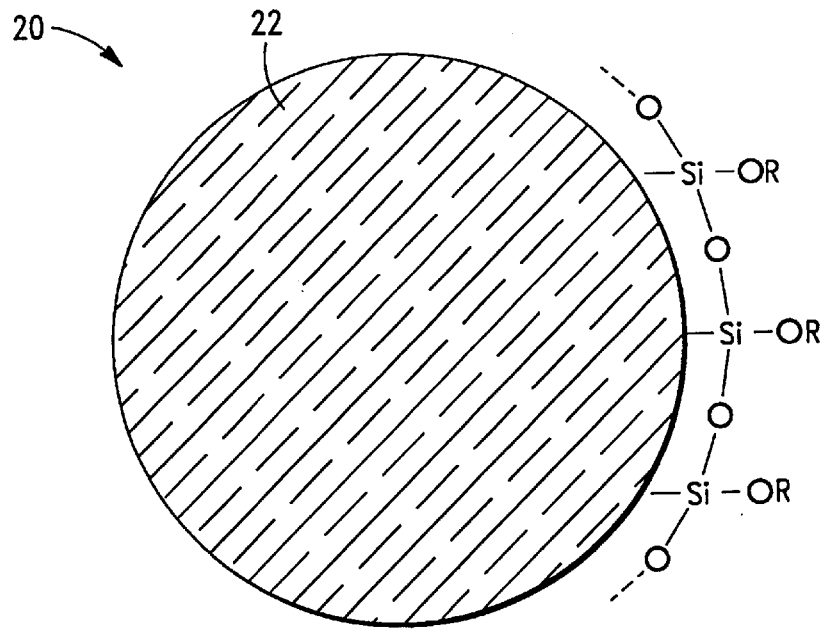
FIG.—11
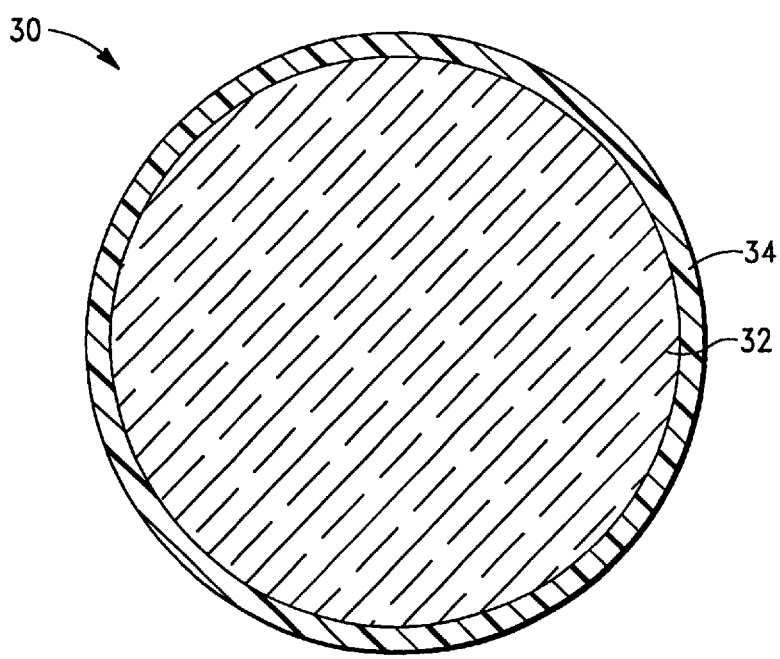
FIG.—12

BAND ARRAY DISPLAY OF POLYNUCLEOTIDE SEPARATIONS

CROSS REFERENCE TO RELATED APPLICATIONS

This application claims priority from the following copending, commonly assigned provisional patent applications, each filed under 35 U.S.C. §111 (b), all of which are incorporated herein by reference:

Ser. No. 60/041,095, filed Mar. 14, 1997
Ser. No. 60/077,875 filed Mar. 13, 1998.
Ser. No. 60/077,998 filed Mar. 13, 1998.

FIELD OF THE INVENTION

This invention relates to a method and system for improved band array displays of double stranded nucleic acid separations. More specifically, the invention is directed toward producing linear array displays of bands representing separated double stranded nucleic acid fragments.

BACKGROUND OF THE INVENTION

Mixtures of double stranded nucleic acid fragments are separated for numerous and diverse reasons ranging from forensic investigations to gene mapping. The traditional and most widely used method for separating mixtures of DNA and other double stranded nucleic acid fragments is slab gel electrophoresis (GEP). Separation of double stranded nucleic acid fragment mixtures by this classical method produces a linear array of bands, wherein each band in the array represents a separated double stranded nucleic acid component of that mixture. Since many mixtures are typically separated and analyzed simultaneously in separate lanes on the same gel slab, a parallel series of such linear arrays of bands is produced. In principle, this is a highly desirable display format because it permits the observer to readily compare many separated mixtures simultaneously. The presence or absence of any band in one linear array compared to another is easily discernible if the separations are visible on the display.

However, in practice, GEP display methodology suffers from serious deficiencies which are inherent in the method.

Bands are often curved rather than straight, their mobility and shape can change across the width of the gel and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results. In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

Linear band arrays representing components of double stranded nucleic acid mixtures which have been separated by GEP have been visualized by a variety of methods, including fluorescence, direct visualization by use of a chemical stain, by adding a dye to the gel which makes the bands visible, or by tagging the DNA with radioactive P-32 before GEP separation, followed by autoradiography. These visualization methods produce a display consisting of parallel linear arrays of bands, which is a direct hard copy representation of the gel slab itself. Separation displays produced in this manner can be distorted and inaccurate because the margins of bands so displayed often are fuzzy and diffuse, rather than being sharply defined. In the autoradiography technique, for example, the radiation emitted from the separated nucleotide components in each band is omnidirectional. This causes the exposure area of the film in contact with the gel slab to be greater than that represented by the actual band dimensions, resulting in a broadened and fuzzy display.

Analyzing adjacent bands in such displays can be a serious problem, especially when there is a large difference in the relative concentration of double stranded nucleic acid present in each band. In such a case the stronger band can obscure the weaker band and the latter may not be visible. Since the displayed data is fixed, it cannot be enhanced, optimized or manipulated, and important information can often go unnoticed. The only way to improve a defective or inadequate separation display is to re-run the separation using a more dilute sample or weaker stain. This is extremely time consuming since gel electrophoresis separations can take up to five hours or more.

A clear need, therefore, exists for an improved and flexible band array display format for double stranded nucleic acid separations in general, and DNA and RNA separations in particular, which can be electronically optimized, quantitated, and stored.

BRIEF SUMMARY OF THE INVENTION

In a first aspect the invention provides a method of representing double stranded nucleic acid fragments which have been separated by Matched Ion Polynucleotide Chromatography as an array of bands, the method comprising providing a digitized signal corresponding to the double stranded nucleic acid fragments in the fractions; and converting the digitized signal into an of array of bands. In a second aspect the invention provides an apparatus for representing double stranded nucleic acid fragments which have been separated by Matched Ion Polynucleotide Chromatography as an array of bands, the apparatus comprising acquisition means for acquiring a digitized signal, the digitized signal corresponding to the double stranded nucleic acid fragments in the fractions, conversion means, for converting the digitized signal to an array of bands corresponding to the double stranded nucleic acid fragments in the fractions, and display means for displaying the array of bands.

In a preferred embodiment of the invention, an analog signal output from the Matched Ion Polynucleotide Chromatography separation process is analog-to-digital (A/D) converted and the digitized signal is input to a computer. In the computer, the digitized signal is converted to a linear array of bands which may be displayed on a video display terminal (VDT), printer or other output device.

The bands may be displayed as lines or rectangles of fixed width. The intensity and/or color of a band may correlate to the amount of double stranded nucleic acid in the respective fraction or the respective double stranded nucleic acid fragment above a user selected threshold level at a corresponding point in the digitized signal.

BRIEF DESCRIPTION OF DRAWINGS

FIG. 1 is a schematic representation of an embodiment of a system for producing band array displays according to the invention.

FIG. 2 illustrates a sample signal representative of an analog output from a detector in an embodiment of a system for producing band array displays according to the invention.

FIG. 3 is an illustration of the conversion of peaks in a sample signal to a band representation according to the invention.

FIG. 4 is an illustration of a gray scale band according to the invention.

FIG. 5 is a flow chart depicting an embodiment of the conversion of peaks in a sample signal to a band representation wherein the bands are represented as rectangles.

FIG. 11 is a schematic drawing of a cross-section of a representation of a reverse phase bead with a silica core and endcapping shielding.

FIG. 12 is a schematic drawing of a cross-section of a representation of a reverse phase bead with a silica core and polymer shielding.

DETAILED DESCRIPTION OF THE INVENTION

The invention produces improved linear array displays of bands representing separations of double stranded nucleic acid mixtures, wherein each band in an array represents a component fragment of the mixture. The band array displays are produced from graphical representations of digitized data.

A linear band array is a preferred format for displaying and viewing double stranded nucleic acid, and especially DNA, separation results since this is the display format of GEP, the most widely used double stranded nucleic acid separation process. A linear band array display generated from digitized data obtained from chromatographic separations, which can be accurately quantified, optimized and stored has not, heretofore been disclosed.

Recently, mixtures of double stranded nucleic acid fragments have been separated on a non polar polymeric stationary phase as described in detail in U.S. Pat. No. 5,585,263 to G. Bonn et. al. which is incorporated by reference in its entirety herein. A major improvement in the scope and utility of the foregoing separation methodology, called Matched Ion Polynucleotide Chromatography (MIPC) has been disclosed in copending applications Ser. No. 748,376 filed Nov. 13, 1996, and now U.S. Pat. No. 5,772,889. Separation of mixtures of double stranded nucleic acid fragments by MIPC may be further enhanced by removal of metal and metal ion contaminants as described in copending application.

In its most general form, the subject matter of the present invention is the separation of polynucleotides utilizing columns filled with nonporous polymeric beads having an average diameter of about 0.5–100 microns; preferably, 1–10 microns; more preferably, 1–5 microns. Beads having an average diameter of 1.0–3.0 microns are most preferred.

In U.S. Pat. No. 5,585,236, Bonn et al. had characterized the nucleic acid separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counter ion agents, and an organic solvent to desorb the nucleic acid from the beads, and wherein the beads are characterized as having a DNA Separation Factor of at least 0.25.

Figure 10:
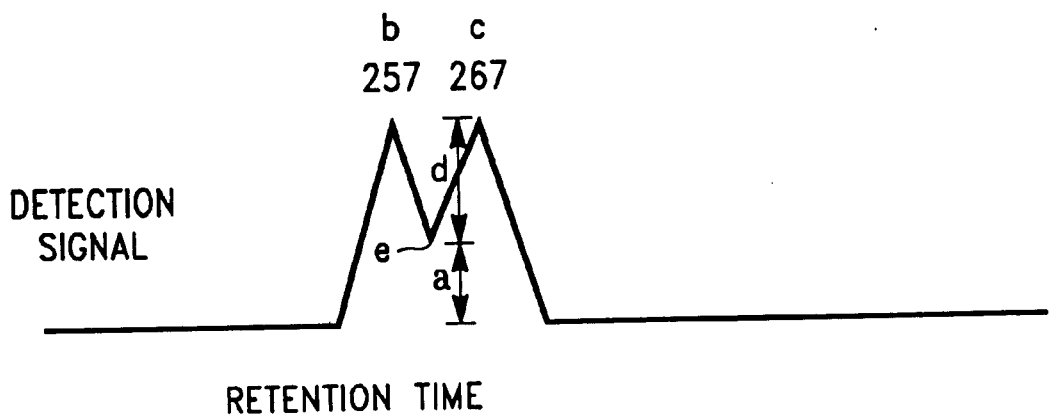
FIG. 10 is a schematic representation of how the DNA Separation Factor is applied to a separation.
Figure 13:
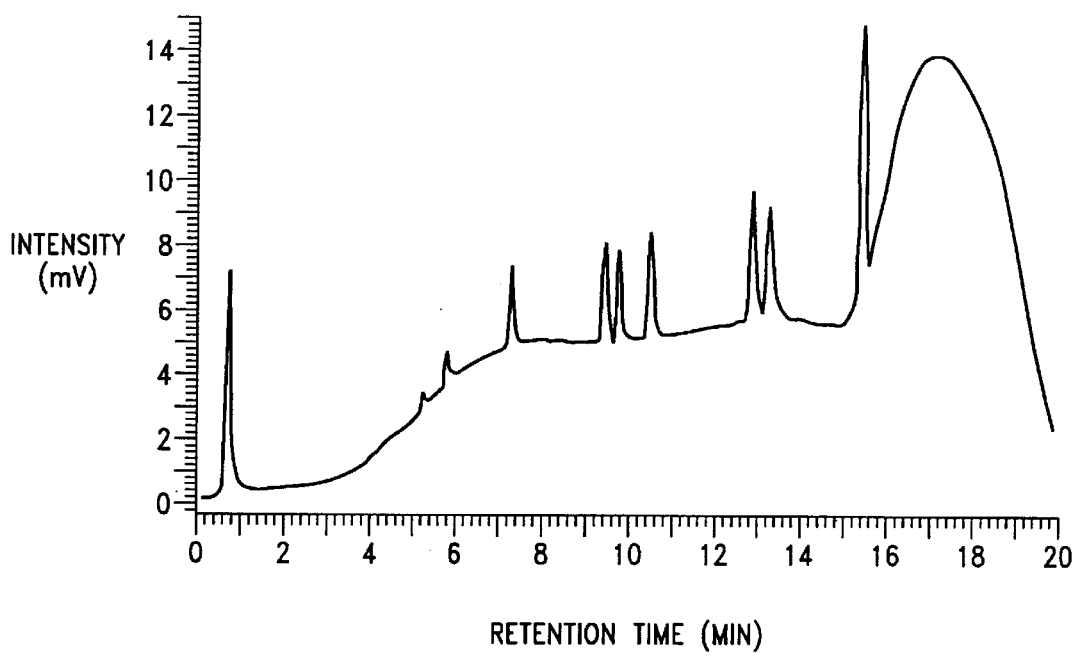
FIG. 13 is a separation of DNA using the process of this invention with non-alkylated poly(styrene-divinylbenzene) particles.

The performance of the beads of the present invention is demonstrated by high efficiency separation by MIPC of double stranded and single stranded DNA. We have found that the best criterion for measuring performance of the beads is a DNA Separation Factor. This is measured as the resolution of 257- and 267-base pair double stranded DNA fragments of a pUC18 DNA-Hae III restriction digest wherein the distance from the valley between the peaks to the top of one of the peaks, over the distance from the baseline to the valley. Referring to the schematic representation of FIG. 10, the DNA Separation Factor is determined by measuring the distance "a" from the baseline to the valley "e" between the peaks "b" and "c" and the distance "d" from the valley "e" to the top of one of the peaks "b" or "c". The DNA Separation Factor is the ratio of d/a. The peaks of 257- and 267-base pairs in this schematic representation are similar in height. The beads of the present invention have a DNA Separation Factor of at least 0.25.

By way of non-limiting theory, we believe that the beads which conform to the DNA Separation Factor as specified herein have a pore size which essentially excludes the polynucleotides being separated from entering the bead. As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required. All beads which provide a DNA Separation Factor of at least 0.25 are intended to be included within the definition of "nonporous" beads.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIDC process.

Pores are open structures through which eluent and other materials can enter the bead structure. Pores are often interconnected so that fluid entering one pore can exit from another pore. We believe that pores having dimensions that allow movement of the polynucleotide into the bead structure result in poorly resolved separations or separations that have very long retention times. In MIDC, however, the beads are "nonporous" and the polynucleotides do not enter the bead structure.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

The nonporous polymeric beads of the present invention are prepared by a two-step process in which small seed beads are initially produced by emulsion polymerization of suitable polymerizable monomers. The emulsion polymerization procedure of the invention is a modification of the procedure of Goodwin et al. (J. W. Goodwin, J. Hearn, C. C. Ho and R. H. Ottweill, Colloid & Polymer Sci., (1974), 252:464–471). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with methyl or ethyl groups or with a hydrocarbon polymer group or can be used in its unmodified state. The polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term "hydrocarbon" as used herein is defined to include alkyl and alkyl substituted aryl groups, having from 1 to 1,000,000 carbons, the alkyl groups including straight chained, branch chained, cyclic, saturated, unsaturated nonionic functional groups of various types including cyano, ester, ether, alkyl groups, and the aryl groups including as monocyclic, bicyclic, and tricyclic aromatic hydrocarbon groups including phenyl, naphthyl, and the like. Methods for hydrocarbon substitution are conventional and well-known in the art and are not an aspect of this invention. The term "hydrocarbon polymer" as used herein is defined to be a polymer having a hydrocarbon composition and from 23 to 1,000,000 carbons.

The chromatographic material reported in the Bonn patent was limited to nonporous beads substituted with alkyl groups having at least 3 carbons because Bonn et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

In the present invention, it has now been surprisingly discovered that successful separation of double stranded DNA can be achieved using underivatized nonporous beads as well as using beads derivatized with methyl, ethyl, or hydrocarbon polymer substitution.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; polymethyl syloxane; polyalkyl siloxane; polydialkyl siloxane; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, must provide a nonporous, non-reactive, and non-polar surface for the Matched Ion Polynucleotide Chromatographic separation.

The beads of the present invention are characterized by having been subjected to precautions during production, including an acid treatment step, designed to substantially eliminate any metal or other contaminants. Only very pure, non-metal containing materials should be used in the production of the beads in order that the resulting beads will have minimum metal content.

In addition to the beads themselves being substantially metal-free, we have also found that, to achieve optimum peak separation during MIPC, the separation column and all process solutions held within the column or flowing through the column should be substantially free of multivalent cation contaminants. As described in commonly owned, co-pending U.S. application Ser. No. 08/748,376 (filed Nov. 13, 1996), this can be achieved by supplying and feeding solutions entering the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer.

Metals found in stainless steel, for example, do not harm the separation, unless they are in an oxidized or colloidal partially oxidized state. For example, 316 stainless steel frits are acceptable in column hardware, but surface oxidized stainless steel frits harm the DNA separation.

For additional protection, multivalent cations in eluent solutions and sample solutions entering the column can be removed by contacting these solutions with multivalent cation capture resin before the solutions enter the column to protect the resin bed from multivalent cation contamination. The multivalent capture resin is preferably cation exchange resin and/or chelating resin.

The beads of the invention comprise a nonporous particle which has non-polar molecules or a non-polar polymer attached to or coated on its surface. In general, the beads comprise nonporous particles which have been coated with a polymer or which have substantially all polar groups reacted with a non-polar hydrocarbon or substituted hydrocarbon group, and any remaining polar groups endcapped with a tri(lower alkyl)chlorosilane or tetra(lower alkyl) dichlorodisilazane as described above.

The nonporous particle is preferably an inorganic particle, but can be a nonporous organic particle. The nonporous particle can be, for example, silica, titanium oxide, aluminum oxide, zirconium oxide, carbon, insoluble polysaccharides such as cellulose, or diatomaceous earth, which has been modified to be nonporous. The nonporous particle is prepared by known procedures. The preferred particle size is about 0.5–100 microns; preferably, 1–10 microns; more preferably, 1–5 microns. Beads having an average diameter of 1.0–3.0 microns are most preferred.

Because the chemistry of preparing conventional silica-based reverse phase HPLC materials is well-known, most of the description of the beads of the invention herein is presented in reference to silica. It is to be understood, however, that other nonporous particles, such as those listed above, can be modified in the same manner and substituted for silica in the process of the invention. For a description of the general chemistry of silica, see Poole, Colin F. and Salwa K. Poole, *Chromatography Today*, Elsevier:New York (1991), pp. 313–342 and Snyder, R. L. and J. J. Kirkland, *Introduction to Modern Liquid Chromatography*, 2nd ed., John Wiley & Sons, Inc.:New York (1979), pp. 272–278, the disclosures of which are hereby incorporated herein by reference in their entireties.

The nonporous beads of the invention are characterized by having minimum exposed silanol groups after reaction with the coating or alkylation reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column. Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based eluent. Hydrolysis will increase the polarity and reactivity of the stationary phase by exposing more silanol sites, or by exposing metals that can be present in the silica core. Hydrolysis will be more prevalent with increased silanol groups. The effect of silanol groups on the DNA separation depends on which mechanism of interference is most prevalent. For example, iron (III) can become attached to the exposed silanol sites, depending on whether the iron (III) is present in the eluent, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8 $\mu$moles of silanol groups per square meter of surface. At best, because of steric considerations, a maximum of about 4.5 μmoles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1–2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. ller in *The Chemistry of Silica, Solubility, Polymerization, Colloid and Surface Properties, and Biochemistry*, John Wiley & Sons:New York (1979).

W. Stöber et al. described controlled growth of monodisperse silica spheres in the micron size range in *J. Colloid and Interface Sci.*, 26:62–69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 μm to 2 μm in diameter.

Nonporous silica core beads can be obtained from Micra Scientific (Northbrook, Ill.) and from Chemie Uetikkon (Lausanne, Switzerland).

To prepare the nonporous beads of the invention, the nonporous particle is coated with a polymer or reacted and endcapped so that substantially all polar groups of the nonporous particle are blocked with a non-polar hydrocarbon or substituted hydrocarbon group. This can be accomplished by several methods.

The organic bonded-phase siloxane coating can be made as a monomolecular layer or as a polymerized multilayer coating. Packings with so-called monomolecular organic layers are normally prepared by reacting the surface silanol groups of siliceous-base particles with mono-, di-, or trifunctional chloro-, dimethyl-, amino-, siloxy-, or alkoxy-silanes. Typical monofunctional reactants used in these reactions include X—Si—R, where X=Cl, OH, OCH$_3$, or OC$_2$H$_5$, and R is an organic radical. FIG. 11 is a schematic representation of a bead 20 having a silica core 22 and a monomolecular organic layer.

Using bi- and trifunctional reactants, such as R$_2$SiX$_2$ and RSiX$_3$, for the surface modifications, up to two Si—X groups per bonded functional group remain unreacted. After treatment with water, hydrolysis of these unreacted groups takes place, and additional silanol groups are formed (sometimes in a polymer matrix) in about the same concentration as the bonded organic functional groups present in the packing. These acidic organo-silanol groups can significantly affect the retention behavior of solutes and adversely influence the stability of the packing in aqueous solutions at pH>7.

Thus, incomplete reaction of the surface with the silane reagent, or the formation of new Si—OH groups from using bi- or trifunctional modifiers, can result in a population of residual acidic Si—OH groups that are readily accessible to molecules of the mobile phase or sample. Therefore, the recent trend is toward (a) a dense monolayer of functional groups instead of partial coverage and (b) the use of monofunctional dimethylsilanes [X—Si(CH$_3$)$_2$—R] to provide a homogeneous organic coating with a minimum possibility of residual Si—OH groups. Monochlorosilane reagents are preferred, if the required organic functionality can be prepared. If two of the R groups in the monofunctional modifier are methyl, surface coverage can be as high as about 4 μmoles per square meter of organic (based on carbon analysis). In the latter case, residual Si—OH groups on the silica surface are unavailable for chromatographic interactions with most solutes because of steric shielding.

The reaction of organosilanols (e.g., HO—Si—R$_3$) or organoalkoxy- (e.g., RO—Si—R$_3$) silanes with silica supports without polymerization can also produce good packings. These reactions are relatively reproducible, provided that traces of water or other reactive species are absent. Unreacted, accessible silanols can be left after the initial reaction, but these can be removed by capping of the packing with chlorotrimethylsilane (providing the R groups do not react with the latter silane).

According to one method, the nonporous particle is coated with a polymer coating. Suitable polymers for use in coating the particle include chain reaction polymers and step reaction polymers, for example, polystyrene, polymethacrylate, polyethylene, polyurethane, polypropylene, polyamide, insoluble polysaccharides such as cellulose, polydimethyl siloxane, polydialkyl siloxane, and related materials. The polymer coating can be attached to the nonporous particle by means of a multi-coating process so that complete shielding of the surface is achieved.

In the last few years, new bonded phase packings, known as polymer-coated or polymer-encapsulated packings, have been introduced based on techniques used to prepare immobilized stationary phases for open tubular column gas chromatography. In this case, the phases are prepared by mechanically coating either bare silica or presilanized silica microparticles with a poly(siloxane) or poly(butadiene) prepolymer, which is then immobilized by peroxide, azo-tert-butane, or gamma radiation-induced chemical crosslinking reactions. FIG. 12 is a schematic illustration of a coated bead 30 having a silica core 32 and polymer coating 34.

An alternative method comprises a combination of covalent bonding with a vinyl-containing silane molecule and then polymerizing a coating on the surface of the particles. A second coating can be applied if residual silanol groups or metal groups are present.

In a variation of this method, the silica surface is first modified by reaction with vinyltrichlorosilane, followed by polymerizing acrylic acid derivatives to and over the derivatized silica surface. The availability of a large number of useful monomers and prepolymers has enabled a wide variety of reverse phase, polar, and ion exchange packings to be prepared using the same general reaction. Also, since the general approach does not depend on the chemistry of the underlying substrate, materials other than silica, for example, alumina and zirconia, can be modified and used under conditions for which silica is unsuitable, for example, with mobile phases outside the pH range 2–7.5. Returning to silica, presilanization decreases the number of active silanol groups, which are then further shielded by the polymeric film anchored over the surface. In reverse phase liquid chromatography, these packings have shown improved chromatographic properties compared to monomeric, chemically bonded phases for the separation of basic solutes. Polymer-encapsulated packings have a film thickness of about 1 nm to maintain reasonable mass transfer characteristics. A description of the this procedure has been published by H. Engelhart et al. (Chromatographia, 27:535 (1989)).

The polymer-coated beads prepared according to either of the above methods can be used in their unmodified state or can be modified by substitution with a hydrocarbon group. Any hydrocarbon group is suitable. The term "hydrocarbon" as used herein is defined to include alkyl and alkyl substituted aryl groups, having from 1 to 100 carbons, the alkyl groups including straight chained, branch chained, cyclic, saturated, unsaturated alkyl groups, and the aryl groups including as monocyclic, bicyclic, and tricyclic aromatic hydrocarbon groups including phenyl, naphthyl, and the like. Methods for hydrocarbon substitution are conventional and well-known in the art and are not an aspect of this invention. The preferred hydrocarbon groups are alkyl groups, and the description of suitable substitution processes hereinbelow are presented as alkylation for purposes of simplification and not by way of limitation, it being understood that aryl substitution by conventional procedures are also intended to be included within the scope of this invention.

The polymer-coated beads can be alkylated by reaction with the corresponding alkyl halide such as the alkyl iodide. Alkylation is achieved by mixing the polymer-coated beads with an alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. Substitution with hydrocarbon groups having from 1 to 1,000,000 and preferably from 1 to 22 carbons can be effected by these processes. Hydrocarbon groups having from 23 to 1,000,000 carbons are referenced herein as hydrocarbon polymers.

Alkylation can be accomplished by a number of known synthesis procedures. These include Friedel-Crafts alkylation with an alkyl halide, attachment of an alkyl alcohol to a chloromethylated bead to form an ether, etc. Although the preferred method for alkylating the polymer-coated beads of the present invention is alkylation after the polymer coating has been formed on the nonporous particle, an alternative method of alkylation is to polymerize alkylated monomers to form an alkylated polymer coating on the nonporous particle. In this embodiment, the monomers will be substituted with alkyl groups having any number of carbon atoms, for example, from 1 to 100, 1 to 50 or 1 to 24, for example, depending upon the requirements of the separation variables.

As an alternative to polymer coating, the nonporous particle can be functionalized with an alkyl group or other non-polar functional group including cyano, ester, and other non-ionic groups, followed by a complete endcapping process to reduce silanol and metal interaction. Endcapping of the nonporous particle can be achieved by reacting the particle with trialkyl chlorosilane or tetraalkyl dichlorodisilazane, such as, for example, trimethyl chlorosilane or dichlorotetraisopropyl-disilazane.

A large number of factors influence the success of the bonding reactions and the quality of the final bonded-phase product. The rate and extent of the bonding reaction depends on the reactivity of the silane, choice of solvent and catalyst, time, temperature, and the ratio of reagents to substrate. Reactive organosilanes with Cl, OH, OR, $N(CH_3)_2$, $OCOCF_3$, and enolates as leaving groups have been widely used. The dimethylamine, trifluoroacetate, and enol ethers of pentane-2,4-dione are the most reactive leaving groups, although economy, availability, and familiarity result in the chlorosilanes and alkoxysilanes being the most widely used, particularly among commercial manufacturers. Initially, reactions can be almost stoichiometric but, as the surface coverage approaches a maximum value, the reaction becomes very slow. For this reason, reaction times tend to be long (12–72 hours), reaction temperatures moderately high (in most cases, around 100° C.) and, in the case of chlorosilanes, an acid acceptor catalyst (e.g., pyridine) is used. Some reagents, such as the alkylsilyl enolates and alkylsilylidimethylamines, do not require additional catalyst, or even solvent, to carry out the reaction. The most common solvents employed are toluene and xylene, although other solvents, such as carbon tetrachloride, trichloroethane, and dimethylformamide (DMF), have been recommended as being superior. Since the bonding reactions are carried out by refluxing in an inert atmosphere, solvents are often selected based on their capacity to be a good solvent for the organosilanes and to attain the desired reaction temperature at reflux. Except for 3-cyanopropylsiloxane bonded phases, the high reactivity of chlorosilanes towards certain polar functional groups (e.g., OH, etc.) precludes their use for the preparation of polar, reverse phase bonded phases. Alkoxysilanes containing acidic or basic functional groups are autocatalytic and the bonded phases are usually prepared by refluxing the silane in an inert solvent at a temperature high enough to distill off the alcohol formed by the condensation reaction with the surface silanol groups. Bonding of neutral, polar ligands generally requires the addition of a catalyst, such as toluene-4-sulfonic acid or triethylamine, in the presence of sufficient water to generate monolayer coverage of the silica. The presence of water speeds up the hydrolysis of the alkoxy groups of the adsorbed organosilane, which tends to react with surface silanol groups rather than polymerize in solution. It seems to be a general problem in the preparation of polar bonded phases that surface silanol groups are blocked by physically adsorbed organosilanes, giving rise to a lower bonded phase density after workup than the maximum theoretically predicted. The bonded phase density can be increased by repeating the reaction a second time or exposed silanol groups minimized by end-capping.

Although most bonded phases are prepared from organosilanes containing a single functionalized ligand bonded to silicon, with the remaining groups being leaving groups and/or methyl groups, more highly substituted organosilanes can also be used. Bifunctional organosilanes, such as 1,3-dichlorotetraisopropyldisilazane, are able to react with surface silanol groups at both ends of the chain, forming a bonded phase that is more hydrolytically stable than bonded phases formed from conventional organosilanes. The bidentate organosilanes have reactive sites that more closely match the spacing of the silanol groups on the silica surface and provide a higher bonded phase coverage than is achieved with dichlorosilanes with both leaving groups attached to the same silicon atom. For alkyldimethylsilanes, increasing the length of the alkyl group increases the hydrolytic stability of the bonded phase relative to that of the trimethylsilyl bonded ligands. Increasing the chain length of the methyl groups increases the hydrolytic stability of the bonded phase, but reduces the phase coverage due to steric effects. The use of monofunctional organosilanes containing one or two bulky groups, for example, isopropyl or t-butyl, on the silicon atom of the silane can become more important in the preparation of bonded phases for use at low pH. The bulky alkyl groups provide better steric protection to the hydrolytically sensitive siloxane groups on the packing surface than does the methyl group.

The general process of coating and endcapping of a silica substrate is well-known technology. However, the general understanding of those who have used these materials is they are not suitable for high performance double stranded DNA separations. However, the beads of this invention are formed by a more careful application of the coating and end-capping procedures to effect a thorough shielding of the silica core, the resulting beads having the ability to perform rapid separations of both single stranded and double stranded DNA which are equal to or better than those achieved using the alkylated nonporous polymer beads disclosed in U.S. Pat. No. 5,585,236, for example.

The beads of the invention are also characterized by having low amounts of metal contaminants or other contaminants that can bind DNA. Whichever method is used to produce the beads of the invention, only very pure, non-metal containing materials should be used in the production of the beads in order that the resulting beads will have minimum metal content. Care must be taken during the preparation of the beads to ensure that the surface of the beads has minimum silanol or metal oxide exposure and that the surface remains nonporous.

To achieve high resolution chromatographic separations of polynucleotides, it is generally necessary to tightly pack the chromatographic column with the solid phase polymer beads. Any known method of packing the column with a column packing material can be used in the present invention to obtain adequate high resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonification are typically used to improve packing density.

For example, to pack a 4.6×50 mm i.d. column, 2.0 grams of beads can be suspended in 10 mL of methanol with the aid of sonification. The suspension is then packed into the column using 50 mLs of methanol at 8,000 psi of pressure. This improves the density of the packed bed.

The separation method of the invention is generally applicable to the chromatographic separation of single stranded and double stranded polynucleotides of DNA and RNA. Samples containing mixtures of polynucleotides can result from total synthesis of polynucleotides, cleavage of DNA or RNA with restriction endonucleases or with other enzymes or chemicals, as well as nucleic acid samples which have been multiplied and amplified using polymerase chain reaction techniques.

The method of the present invention can be used to separate double stranded polynucleotides having up to about 1500–2000 base pairs, although in most cases, the method will be used to separate polynucleotides having up to about 600 base pairs or fewer. The method provides good separation for longer polynucleotides having about 80–600 base pairs, and also for sort polynucleotides having only about 5–80 base pairs.

In a preferred embodiment, the separation is by Matched Ion Polynucleotide Chromatography (MIPC). The nonporous beads of the invention are used as a reverse phase material that will function with counter ion agents and a solvent gradient to produce the DNA separations. In MIPC, the polynucleotides are paired with a counter ion and then subjected to reverse phase chromatography using the nonporous beads of the present invention. Counter ion agents that are volatile, such as trialkylamine acetate, trialkylamine carbonate, bis(trialkylamine) hydrogen phosphate (TEA$_2$HPO$_4$), etc., are preferred for use in the method of the invention, with triethylammonium acetate (TEAA) and triethylammonium hexafluoroisopropyl alcohol being most preferred.

To achieve optimum peak resolution during the separation of DNA by MIPC using the beads of the invention, the method is preferably performed at a temperature within the range of 20° C. to 90° C.; more preferably, 30° C. to 80° C.; most preferably, 50° C. to 75° C. In general, separation of single-stranded fragments should be performed at higher temperatures.

We have found that the temperature at which the separation is performed affects the choice of solvents used in the separation. One reason is that the solvents affect the temperature at which a double stranded DNA will melt to form two single strands or a partially melted complex of single and double stranded DNA. Some solvents can stabilize the melted structure better than other solvents. The other reason a solvent is important is because it affects the transport of the DNA between the mobile phase and the stationary phase. Acetonitrile and 1-propanol are preferred solvents in these cases. Finally, the toxicity (and cost) of the solvent can be important. In this case, methanol is preferred over acetonitrile and 1-propanol is preferred over methanol.

When the separation is performed at a temperature within the above range, an organic solvent that is water soluble is preferably used, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Solvents which are particularly preferred for use in the method of this invention include methanol, ethanol, 2-propanol, 1-propanol, tetrahydrofuran (THF), and acetonitrile, with acetonitrile being most preferred overall.

We have determined that the chromatographic separations of double stranded DNA fragments exhibit unique Sorption Enthalpies H$_{sorp}$). Two compounds (in this case, DNA fragments of different size) can only be separated if they have different partition coefficients (K). The Nernst partition coefficient is defined as the concentration of an analyte (A) in the stationary phase divided by its concentration in the mobile phase:

$$K = \frac{[A]_s}{[A]_m}$$

The partition coefficient (K) and the retention factor (k) are related through the following equations:

$$K = \frac{n(A)_s V_m}{n(A)_m V_s} \text{ and } k = \frac{n(A)_s}{n(A)_m}$$

the quotient V$_m$/V$_s$ is also called phase volume ratio ($\Phi$). Therefore:

$$k = K\Phi$$

To calculate the sorption enthalpies, the following fundamental thermodynamic equations are necessary:

$$\ln K = -\frac{\Delta G_{sorp}}{RT}, \ln k = -\frac{\Delta G_{sorp}}{RT} + \ln \Phi \text{ and}$$

-continued $$\Delta G_{sorp} = \Delta H_{sorp} - T\Delta S_{sorp}$$

By transforming the last two equations, we obtain the Van't Hoff equation:

$$\ln k = -\frac{\Delta H_{sorp}}{RT} + \frac{\Delta S_{sorp}}{R} + \ln \Phi$$

From a plot ln k versus 1/T, the sorption enthalpy $\Delta H_{sorp}$ can be obtained from the slope of the graph (if a straight line is obtained). $\Delta S_{sorp}$ can be calculated if the phase volume ratio ($\Phi$) is known.

Figure 15:
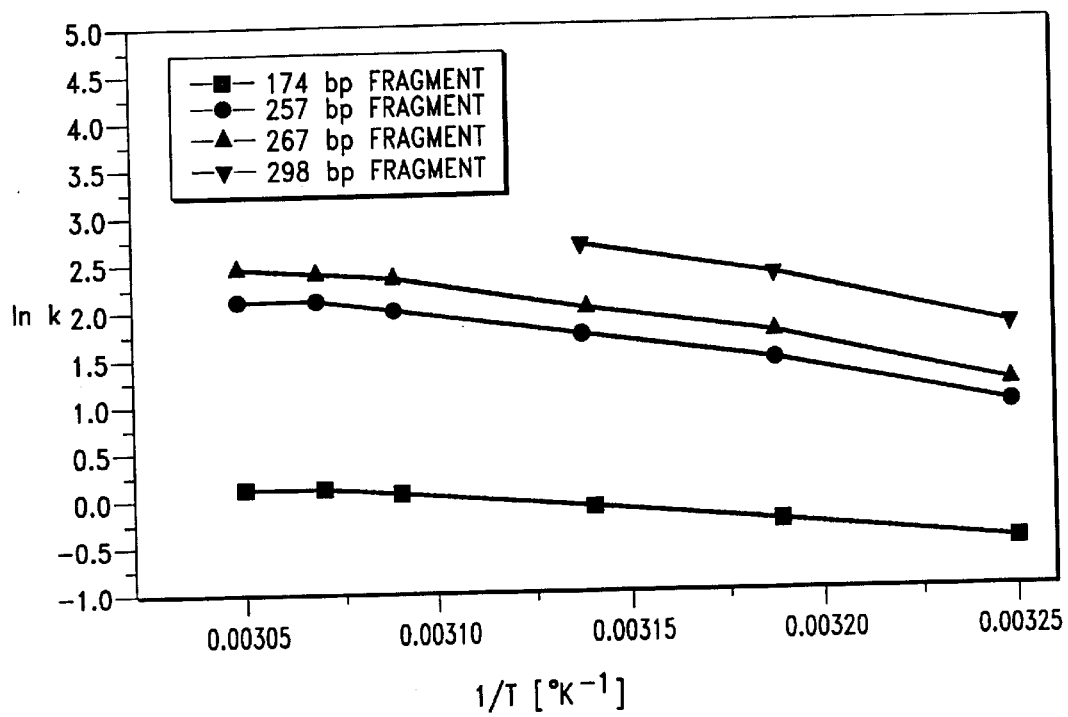
FIG. 15 is a Van't Hoff plot of the retention factor $1/T[°K^{-1}]$ with underivatized poly(styrene-divinylbenzene) beads showing positive enthalpy using acetonitrile as the solvent.
Figure 16:
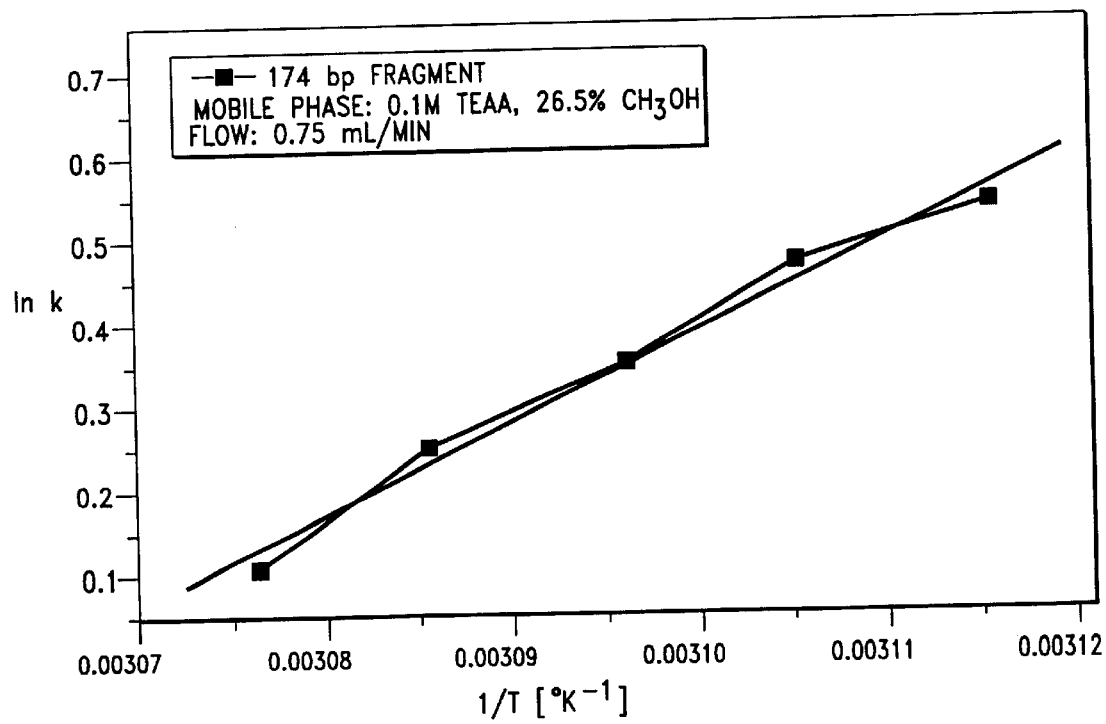
FIG. 16 is a Van't Hoff plot of the retention factor $1/T[°K^{-1}]$ with alkylated poly(styrene-divinylbenzene) beads showing negative enthalpy using methanol as the solvent.

The Sorption Enthalpy $\Delta H_{sorp}$ is positive ($\Delta H_{sorp}>0$) showing the separation is endothermic using acetonitrile as the solvent (FIGS. 14 and 15), and using methanol as the solvent, the Sorption Enthalpy $\Delta H_{sorp}$ is negative ($\Delta H_{sorp}<0$), showing the separation is exothermic (FIG. 16).

The same experiments on silica beads coated with poly (styrene-divinylbenzene) also give a negative slope for a plot of ln k versus 1/T, although the plot is slightly curved.

Other features of the invention will become apparent in the course of the following descriptions of exemplary embodiments which are given for illustration of the invention and are not intended to be limiting thereof.

All publication and granted references cited herein are hereby incorporated by reference in their entirety.

MIPC, as used herein, is defined as a process for separating single and double stranded nucleic acids using non-polar beads having a pore size which is effective to exclude the smallest double stranded nucleic acid being separated, wherein the process uses counter ion agents and an organic solvent to desorb the double stranded nucleic acids from the beads. MIPC separates mixtures of double stranded nucleic acid fragments, double stranded DNA and RNA, on the basis of base pair length and not on the basis of nucleic acid sequence. MIPC is a size based separation. MIPC can be automated and computer controlled. Separations of DNA fragments having 5–1500 base pairs can be effectively achieved in less than 5 minutes. Such separations produce sharp and reproducible results.

MIPC was, therefore, selected as the preferred double stranded nucleic acid separation process for use with the present invention because it provides an ideal technology for producing an accurate linear band array display format, generated from digitized data, which can be electronically optimized and quantified. Other suitable chromatographic processes capable of separating double stranded double stranded nucleic acid fragments may also be used.

FIG. 1 is a schematic representation of an embodiment of a system 2 for producing band array displays according to a first aspect of the invention. The system includes a separation column 4 coupled to a detector 6. The detector has an analog output which is coupled to an A/D converter 8. The A/D converter output is coupled to a CPU 10, e.g. a personal computer (PC). The CPU includes software (not illustrated in FIG. 1) for converting digitized data representing separated double stranded nucleic acid fragments and outputting a graphical representation of a linear array of bands wherein each band corresponds to a separated fragment of the original mixture. It is understood that close-running fragments may not be completely separated in some separations.

The CPU 10 is coupled to a storage device (e.g. hard disk, floppy disk, etc.) 16 for storing data. The CPU 10 may be coupled to a video display terminal (VDT) 18, a printer 20, or other output device (not illustrated) for displaying or otherwise outputting a graphical representation of separated nucleotide fragments. The CPU 10 is also coupled to a keyboard 12 and a pointing device 14, e.g. mouse, trackball, touch pad, etc.

The preferred separation column 4 is packed with beads suitable for MIPC as described in U.S. patent applications Ser. No. 60/077,875 filed Mar. 13, 1998 and Ser. No. 60/077,988 filed Mar. 13, 1998. The preferred detector 6 is an ultra-violet (UV) detector operating at 260 nm, the absorbance maximum of DNA. If the fragments to be detected are tagged with fluorescent or radioactive markers, a fluorescence detector or a radioactivity detector, respectively, may be used. Any detector which is capable of detecting the fragments being separated may be used in the system 2.

The system 2 produces bands having a desired shape which provide both qualitative and quantitative information about the separated components of the double stranded nucleic acid mixture. For example, the preferred shape is a band in the form of a line or elongated rectangle of fixed width. The length, and optionally intensity, of a band, whether a line or a rectangle, is proportional to the absorbance of mixture component represented by the band. The band length, and optionally intensity, is a true and accurate quantitation of a component's relative and absolute concentration since the entire sample represented by a band is seen by the detector. This is in contrast to scanning a gel slab, wherein the detector commonly only sees the center of a band. Since the bands produced by GEP separations are not generally uniform, the data so obtained is neither quantitative nor accurate The operation of the system 2 to produce an array of bands representing the double stranded nucleic acid separation results is as follows. A solution of a mixture of double stranded nucleic acid fragments is separated into its component fragments in the separation column 4 as described in U.S. patent applications Ser. No. 60/077,875 filed Mar. 13, 1998 and Ser. No. 60/077,998 filed Mar. 13, 1998, wherein double stranded nucleic acid fragments are separated on the basis of size, i.e. number of base pairs. The double stranded nucleic acid mixture may be tagged with fluorescent or radioactive markers to enhance the sensitivity of detection without altering the nature of the separation.

A mobile phase solvent capable for separating the double stranded nucleic acid mixture is flowed through the column 4. Although the exact composition of the mobile phase varies with the nature and molecular weight range of the double stranded nucleic acid mixture being separated, the most effective mobile phases contain water, an organic solvent which is completely miscible with water and a counter ion agent. Preferred organic solvents include acetonitrile, tetrahydrofuran and C-1 to C-3 alkanols. Examples of specific mobile phases which have been used to effect double stranded nucleic acid separations, including double stranded DNA separations, are described in U.S. patent applications Ser. No. 60/077,875 filed Mar. 13, 1998 and Ser. No. 60/077,998 filed Mar. 13, 1998.

The column effluent is directed to flow past the detector 6 which is coupled to the column. The detector must be capable of detecting double stranded nucleic acids or tagged analogs thereof. A preferred detector operates using a UV source and UV sensor, and detects the presence of double stranded nucleic acid fragments by measuring the change in UV absorption of the effluent as the effluent flows past the detector. If the double stranded nucleic acid fragments in the mixture to be separated have been tagged with fluorescent or radioactive markers prior to separation, then a fluorescence or radioactivity detector, respectively, can be used.

As the mobile phase flows through the column, it carries the separated double stranded nucleic acid fragments, which elute in order of lower to higher number of base pairs, through the column and past the detector. Under normal circumstances, all of the sample entering the column exits the column and travels through the detector cell. The presence of the double stranded nucleic acids fragments is detected as they flow past the detector, which responds by generating typically an analog output signal, typically an analog varying voltage. The magnitude of the output signal is a function of the quantity and absorbance of the double stranded nucleic acid present in the mobile phase passing the detector at any given time.

The analog output signal of the detector 6 is input to the A/D converter 8 where the signal is digitized, and the digitized signal is input to the CPU 10. The rate at which the A/D converter 8 samples and digitizes the analog output of the detector 6 depends on the flow rate of the mixture through the column 4 and the detector 6, and may optionally be varied. In a preferred embodiment, the A/D converter 8 has a variable sampling rate which can be adjusted to optimize data collection. A generally effective sampling rate is 100 millisecond intervals. If the sampling rate is varied, this is taken into account when the digitized signal is reconstructed in the computer for processing and conversion to a band representation. The digitized signal is received by the CPU 10, and may be stored in the storage device 16 for subsequent processing. The digitized data may be displayed and/or converted and displayed in a band form in real-time and/or off line (i.e. at a later time).

All of the data from the detector are used to display the bands, even if data are manipulated so that a function is used to display some distinct property. For example, the bands may only be shown if a predetermined signal threshold is reached. However, all of the data above this threshold is used to display the band. Absolute concentrations of the separated fragments can be determined by comparing the signal corresponding to a fragment with that of an appropriate standard. For example, standards of known base pair length and concentration may be used to normalize the detector's response to the separated fragments. Optionally, if the double stranded nucleic acid fragment mixture is tagged with a fluorescent or radioactive marker, fluorescent or radioactive standards, respectively, may be used.

FIG. 2 illustrates a sample signal 100 representative of an analog output from the detector 6. The sample signal 100 includes three peaks 102, 104, 106 which represent the output of the detector 6 in response to a mixture containing double stranded nucleic acid fragments of three different base pair lengths. The height of the sample signal 100 represents the instantaneous amount of double stranded nucleic acid fragments flowing past the detector 6 as a function of time. The three peaks 102, 104, 106 represent the amount of double stranded nucleic acid fragments of each of the three respective different base pair lengths detected in the mixture, and the total area under each of the curves of the peaks 102, 104, 106 represents the total amount of double stranded nucleic acid fragments of the three respective different base pair lengths detected in the mixture. The signal 100 illustrated in FIG. 2 and subsequent FIGS. is by way of illustration only, and does not necessarily represent an actual signal output from a detector 6.

FIG. 3 illustrates the conversion of the peaks 102, 104, 106 in the sample signal 100 to a band representation. A reconstructed signal 100' in FIG. 3 represents a signal reconstructed from the digitized values of the original sample signal 100 (FIG. 2). For discussion and display purposes only, the reconstructed signal 100' is shown rotated 90 degrees from how the sample signal 100 is illustrated in FIG. 2. In FIG. 3, time, and hence base pair length, increases from top to bottom, and the amplitude of the reconstructed signal 100' increases to the right.

The graphical, e.g. band, representation of the double stranded nucleic acid fragments may take several forms. For example, in a first array 110, each of the reconstructed peaks 102', 104', 106' is represented by a band in the form of a corresponding line 112, 114, 116, with the vertical position of the lines 112, 114, 116 corresponding to the maximum value of the respective reconstructed peaks 102', 104', 106'. In a second array 120, each of the reconstructed peaks 102', 104', 106' is represented by a band in the form of a rectangle 122, 124, 126, with the vertical position and length (vertical height on the paper) of the respective rectangles 122, 124, 126 corresponding to a first user-selected threshold $T_1$. In a third array 130, each of the reconstructed peaks 102', 104', 106' is represented by a band in the form of a rectangle 132, 134, 136, with the vertical position and length of the respective rectangles 132, 134, 136 corresponding to a second user-selected threshold $T_2$. Since $T_1$ is set at a higher amplitude than $T_2$ on the reconstructed signal 100', each of the bands 122, 124, 126 in the second band array 120 corresponding to $T_1$ has a shorter length than the corresponding bands 132, 134, 136 in the third band array 130 corresponding to $T_2$. The system of the invention provides the user with the ability to select the desired form of band display, e.g. line or rectangle, and also permits the user to vary the threshold to filter out noise or other components in the reconstructed signal 100'.

In addition, if the line or rectangular band representation is chosen, the user may select to display a gray scale, color, or other form of display, where, for example, the intensity of the gray scale, or the color, corresponds to the amplitude of the reconstructed signal. A representative gray scale band 108 is illustrated in FIG. 4.

As also illustrated in FIG. 4, depending on the number of quantization levels available, a gray scale band display may tend to appear as a series of discrete horizontal sub-bands. In a preferred embodiment of the invention, a "blended" gray scale band display (representing an analog variation across the band) is formed by turning individual pixels "on" or "off". In each line of pixels forming the band, the decision to turn each pixel "on" or "off" is derived by multiplying the corresponding amplitude of the reconstructed signal 100' times a random number. If the resulting product is greater than a certain threshold, then a pixel is turned on, i.e. displayed as a black (or color) point. Otherwise, the pixel is not so displayed. Thus, as the amplitude of the reconstructed signal 100' increases, more pixels will be displayed along corresponding lines of the respective band.

Figure 6:
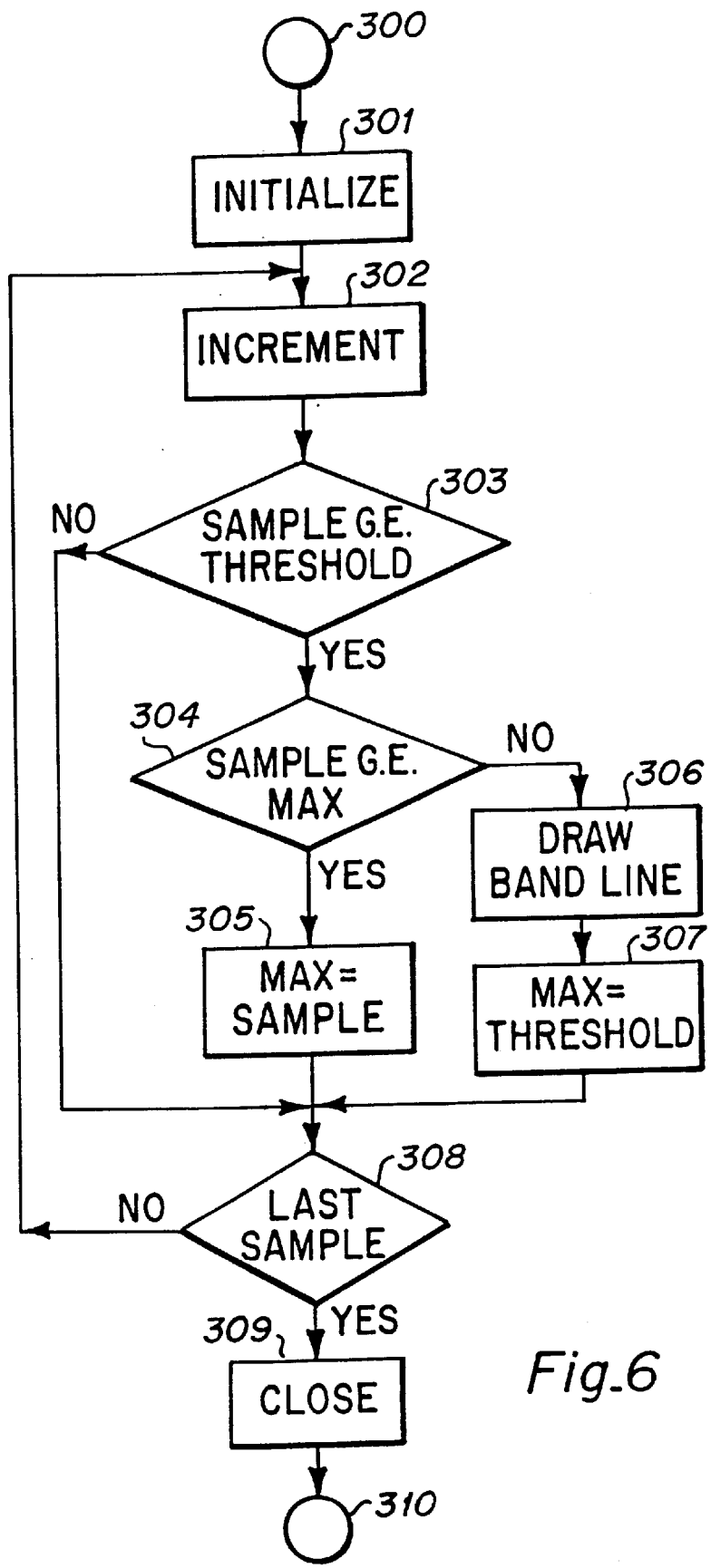
FIG. 6 is a flow chart depicting an embodiment of the conversion of peaks in a sample signal to a band representation wherein the bands are represented as lines.

FIG. 5 is a flow chart depicting an embodiment of the conversion of peaks in a sample signal to a band representation wherein the bands are represented as rectangles. FIG. 6 is a flow chart depicting an embodiment of the conversion of peaks in a sample signal to a band representation wherein the bands are represented as lines. Both flow charts will be described as though the bands are being formed from data which has been previously collected and stored. However, those skilled in the art will readily see that the basic procedures can be used to convert sample signal data to a band representation in real time. Those skilled in the art will also recognize that the flow charts can be drawn in a number of different forms without departing from the scope of the invention.

Prior to entering either flow chart, a user will typically select a rectangle or line representation from a menu selection. Referring first to FIG. 5, the flow begins with an INITIALIZE process block 201 in which counters, desired signal threshold, and other variables are initialized. A sample counter is then incremented by 1 in an INCREMENT COUNTER process block 202. The current sample indicated by the sample counter is compared to the signal threshold in a SAMPLE .GE. THRESHOLD decision block 203. If the current sample is above the threshold, then if the sample is established as the start of a new band, as determined by a NEW BAND decision block 204, a new band is started in a START BAND process block 205. In the START BAND 205 process block, the graphic display output for the band is started and variables are initialized for calculating sample concentration and other relevant quantities. The flow then passes through a LAST SAMPLE decision block 209. Since the amount of eluting solvent used is sufficient to cause all the nucleic acid mixture to pass through the column 4 and detector 6 (FIG. 1), the LAST SAMPLE decision block 209 will always flow through its NO exit if the sample signal is above the threshold (representing fragments then being detected by the detector).

The flow then passes back up to the INCREMENT COUNTER process block 202. Once a band has been started, i.e. the sample signal reaches or exceeds a user specified threshold, and the sample signal remains at or above the threshold, the flow from the NEW BAND 204 decision block flows through its NO exit to an EXTEND BAND process block 206, in which the graphic display output for the band continues and the concentration and other quantities are accumulated. The process continues until the sample signal falls below the threshold which will cause the SAMPLE .GE. THRESHOLD decision block 203 to flow through its NO exit to the IN BAND decision block 207. When the first below threshold sample is encountered after a band has been started, the IN BAND decision block 207 will flow through its YES path to an END BAND 208 process block. In the END BAND process block 208, the graphic display output for the band is terminated at the previous sample (which was at or above the threshold), and the concentration and other relevant quantities are saved for display or other use as selected by the user.

The process continues until the SAMPLE .GE. THRESHOLD decision block 203 flows through its NO exit, the IN BAND decision block 207 flows through its NO exit, and the LAST SAMPLE decision block 209 flows through its YES exit, indicating the last sample of the run.

In the CLOSE process block 210, data summarizing the total concentration and other relevant quantities are calculated, stored, and may be displayed.

As illustrated in FIG. 4 and described above, the bands may be displayed using color, intensity, a blended gray scale using random pixels, and the like to represent the value of the digitized detector signal. This may be implemented, for example, in each of the START BAND 205, EXTEND BAND 206 and END BAND 208 process blocks.

Referring to FIG. 6, the flow begins with an INITIALIZE process block 301 in which variables, counters, desired signal threshold, etc. are initialized. A maximum value is set equal to the selected threshold. A sample counter is then incremented by 1 in an INCREMENT COUNTER process block 302. The current sample is compared to the signal threshold in a SAMPLE .GE. THRESHOLD decision block 303. If the current sample is greater than or equal to the threshold, the current sample is then compared to the maximum value in a SAMPLE .GT. MAX decision block 304. If the current sample is greater than the maximum value, the maximum value is then set to the value of the current sample in a MAX=SAMPLE process block 305. The flow from the MAX=SAMPLE 305 process block proceeds to a LAST SAMPLE 308 decision block. Similar to the arrangement of FIG. 5, the YES exit to the LAST SAMPLE 308 decision block will only be taken after all the nucleic acid mixture passes through the column 4 and detector 6. The flow then passes back up to the INCREMENT process block 302 and continues until the current sample is less than the maximum value, indicating that the signal has reached a peak and is beginning to decline. When this occurs, the process flow out the NO exit to the SAMPLE GE. MAX decision block 304.

In a DRAW BAND LINE process block 306, a band line is displayed in a position corresponding to the peak signal value. The flow passes to a MAX=THRESHOLD process block 307 in which the maximum value is reset to the user selected threshold value.

The process continues until the last sample is reached and the LAST SAMPLE decision block 308 flows through its YES exit.

In the CLOSE process block 309, data summarizing the total concentration and other relevant quantities are calculated, stored, and may be displayed.

In a manner similar to the display of bands as rectangles, the lines may be displayed using color, intensity, a blended gray scale using random pixels, and the like to represent the peak value of the digitized detector signal. This may be implemented in the DRAW BAND LINE process block 306.

In the above description, the band may be displayed as a line positioned according to the peak value of the signal. In instances in which the signal is at a peak value for more than one sample, the line may be drawn in a position corresponding to the initial sample, the last sample, or at a predetermined or user selected position between the first and last samples at the peak value.

Figure 7:
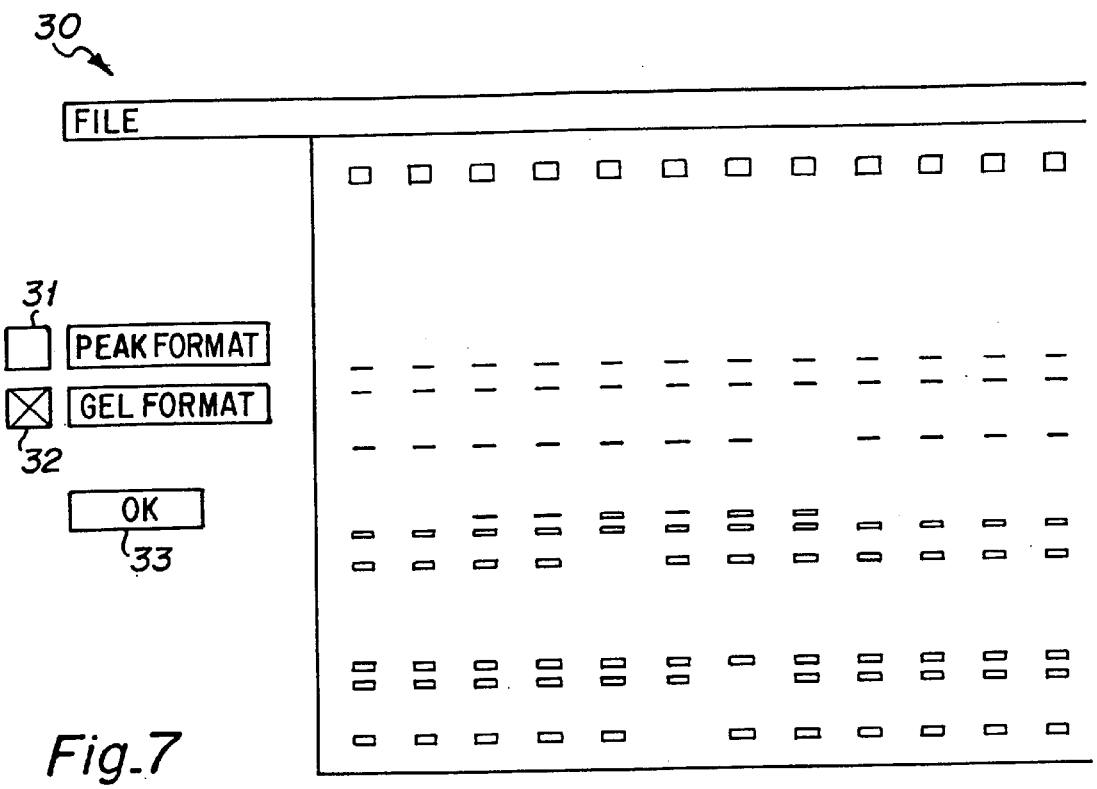
FIGS. 7, 8 and 9 are illustrations of sample displays according to the invention.
Figure 8:
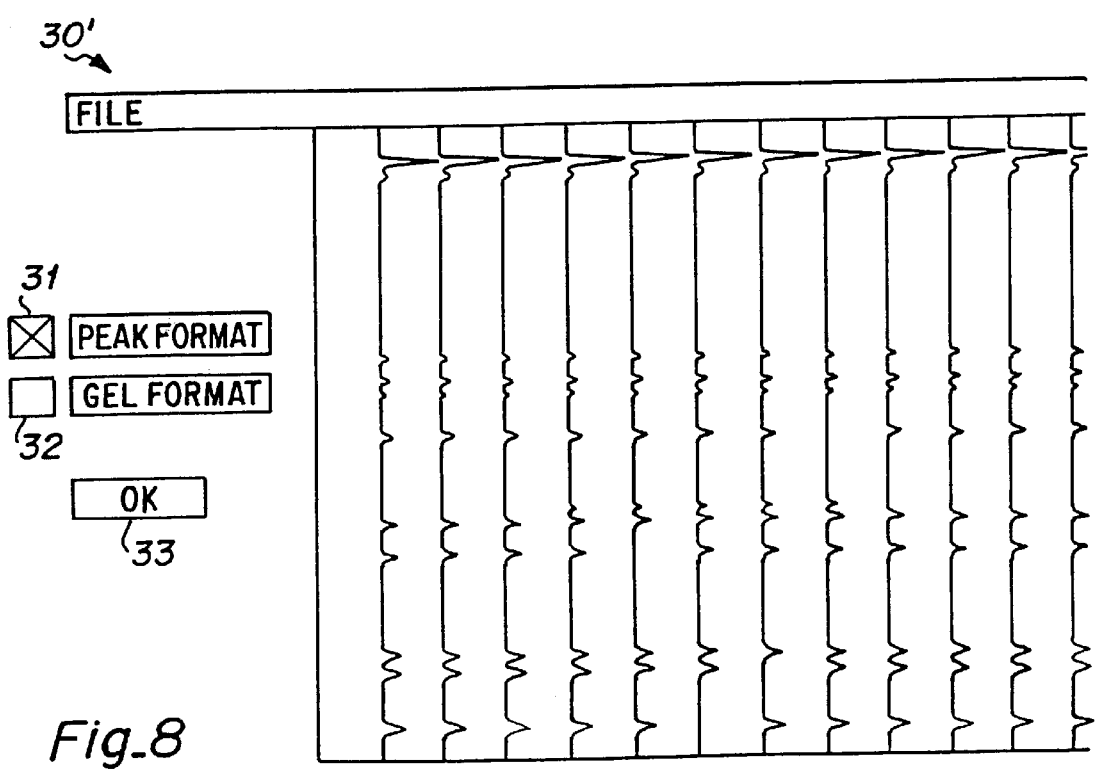
Figure 9:
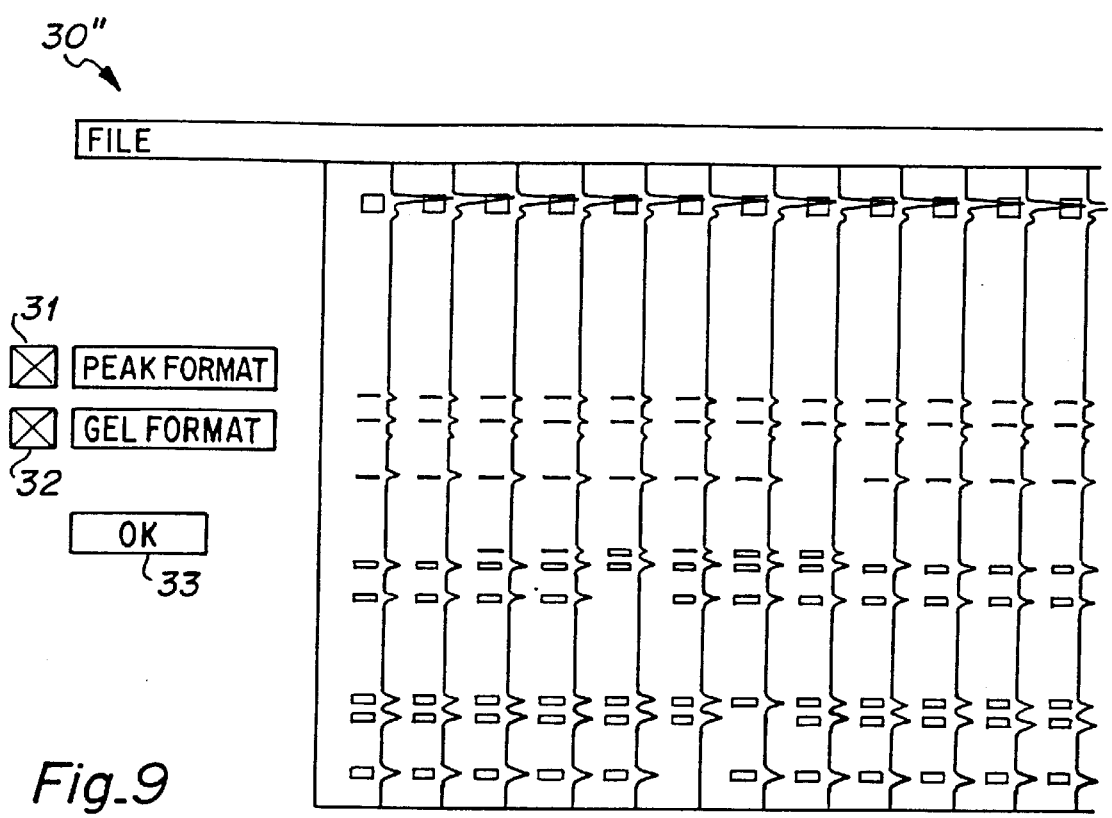

FIGS. 7, 8 and 9 illustrate sample displays that may be output on the VDT 18, printer 20 or other device. The sample displays in FIGS. 7, 8 and 9 are illustrated by way of example only, and do not limit the display format or content provided by the invention. Referring to FIG. 7, in a first sample display window 30 are a series of controls including, e.g., Peak format selection 31, Gel format selection 32, and an OK (or execute) 33 button. Other controls which may be included may include graphics display functions well know to those skilled in the art, e.g. zoom, pan, move (horizontal and/or vertical), rotate, copy, cut, paste, etc. Controls and/or selections may also be enabled using menu driven commands, as is also well known to those skilled in the art. Also illustrated in FIG. 7 are a series of sample band displays corresponding to the Gel format selection 32 control being selected.

The CPU 10 can store data from numerous separations. As illustrated in FIG. 7, multiple stored separations can be displayed simultaneously for comparison of component fragments of one sample to those of another sample. When many separations are displayed simultaneously, the arrays of bands are parallel to each other as shown in FIG. 7. If more separated samples need to be compared than can fit, e.g. on the VDT 18, additional separations can be made to appear by scrolling using conventional techniques, e.g. the pointing device 14 or arrow or page up/page down command keys on the keyboard 12. Referring to FIGS. 3, 4 and 7, bands may be represented as lines or rectangles, and may include color and/or a gray scale. In bands displayed with color and/or gray scale, the color and/or intensity of each band, may be proportional to the concentration of double stranded nucleic acid in the fraction the band represents. Any and all separations may be displayed on the VDT 18 and/or printed by the printer 20 or other output device in any chosen display format.

Referring to FIG. 8, in a second sample display window 30' the Peak format selection 31 control is shown selected and the sampled signals are displayed in band format. In FIG. 9, in a third sample display window 30" both the Peak format selection 31 and Band format selection 32 controls are selected, and the sampled signals are displayed in both peak and band formats.

Using the zoom feature mentioned above, a particular array of bands or a segment thereof can be electronically expanded, to improve the visible resolution between adjacent bands. This feature is particularly important when one band is present in greater concentration than an adjacent band and the more concentrated band obscures the less concentrated band. In gel electrophoresis separations, a close running less concentrated band may go completely unnoticed. When multiple separations are viewed simultaneously, the lane zoom feature can be applied to all the band arrays. A similar manipulation and display may be performed in the peak format if it is chosen for display.

When a separation column is calibrated with a double stranded nucleic acid standard of known base pair length and concentration, the base pair length of the separated fragments of the mixture and their absolute concentrations can be calculated by the software. Because the separation and display methodology is reproducible, accurate base pair lengths of the components of many mixtures can be calculated without the need to recalibrate the system for each separation.

Menu driven commands may be used to generate a variety of qualitative and quantitative information in alphanumeric form, including, but not limited to, integration of separated bands, display of base pair length, absolute concentration and relative percentage of each component fraction in a separated mixture. Bands separated from one sample may also be electronically subtracted from those of another sample to simplify visual determination of the presence or absence of a particular DNA fragment(s) in any separated DNA mixture. Similar operations may be performed if the peak shape is chosen for display.

Procedures described in the past tense in the examples below have been carried out in the laboratory. Procedures described in the present tense have not been carried out in the laboratory, and are constructively reduced to practice with the filing of this application.

EXAMPLE 1

Preparation of Nonporous poly(styrene-divinylbenzene) Particles

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased.

The protocol for the second step is based on the activated swelling method described by Ugelstad et al. (*Adv. Colloid Interface Sci.*, 13:101–140 (1980)). In order to initiate activated swelling, or the second synthetic step, the aqueous suspension of polystyrene seeds (200 ml) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C.

Following the removal of acetone, the swollen beads were further grown by the addition of 310 g of a ethyidivinylbenzene and divinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were washed four times with 100 mL of n-heptane, and then two times with each of the following: 100 mL of diethylether, 100 mL of dioxane, and 100 mL of methanol. Finally, the beads were dried.

EXAMPLE 2

Acid Treatment Step

The beads prepared in example 1 were washed three times with tetrahydrofuran and two times with methanol. Finally the beads were stirred in a mixture containing 100 mL tetrahydrofuran and 100 mL concentrated hydrochloric acid for 12 hours. After this acid treatment, the polymer beads were washed with a tetrahydrofuran/water mixture until neutral (pH=7). The beads were then dried at 40° C. for 12 hours.

EXAMPLE 3

Sorption Enthalpy Measurements

Figure 14:
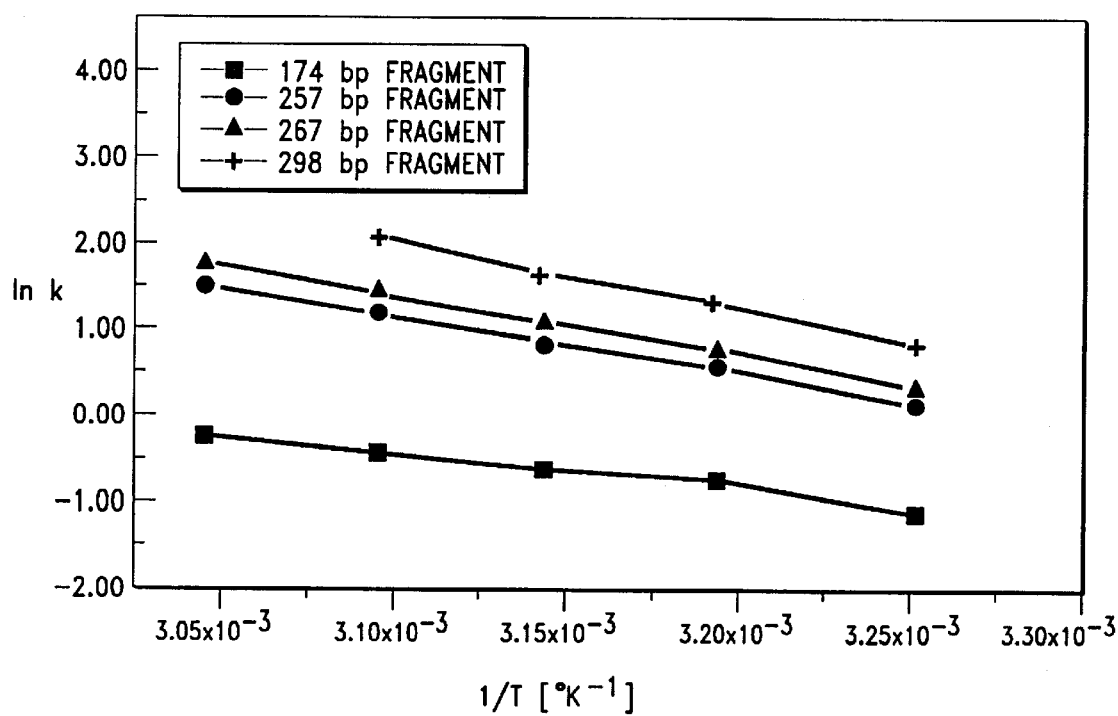
FIG. 14 is a Van't Hoff plot of the retention factor $1/T[°K^{-1}]$ with alkylated poly(styrene-divinylbenzene) beads showing positive enthalpy using acetonitrile as the solvent.

Four fragments (174 base pair, 257 base pair, 267 base pair, and 298 base pair, found in 5 $\mu$L pUC18 DNA-Hae III digest, 0.04 $\mu$g DNA/$\mu$L) were separated under isocratic conditions at different temperatures using octadecyl modified, nonporous poly(styrene-divinylbenzene) polymer beads. The separation was carried out using a Transgenomic WAVE™ DNA Fragment Analysis System equipped with a DNASep™ column (Transgenomic, Inc., San Jose, Calif.)

under the following conditions: Eluent: 0.1 M triethylammonium acetate, 14.25% (v/v) acetonitrile at 0.75 mL/min, detection at 250 nm UV, temperatures at 35, 40, 45, 50, 55, and 60° C., respectively. A plot of ln k versus 1/T shows that the retention factor k is increasing with increasing temperature (FIG. 14). This indicates that the retention mechanism is based on an endothermic process ($\Delta H_{sorp} > 0$).

The same experiments on non-alkylated poly(styrene-divinylbenzene) beads gave a negative slope for a plot of ln k versus 1/T, although the plot is slightly curved (FIG. 15).

The same experiments performed on octadecyl modified, nonporous poly(styrene-divinylbenzene) beads but with methanol replacing the acetonitrile as solvent gave a plot ln k versus 1/T showing the retention factor k is decreasing with increasing temperature (FIG. 16). This indicates the retention mechanism is based on an exothermic process ($\Delta H_{sorp} < 0$).

Figure 17:
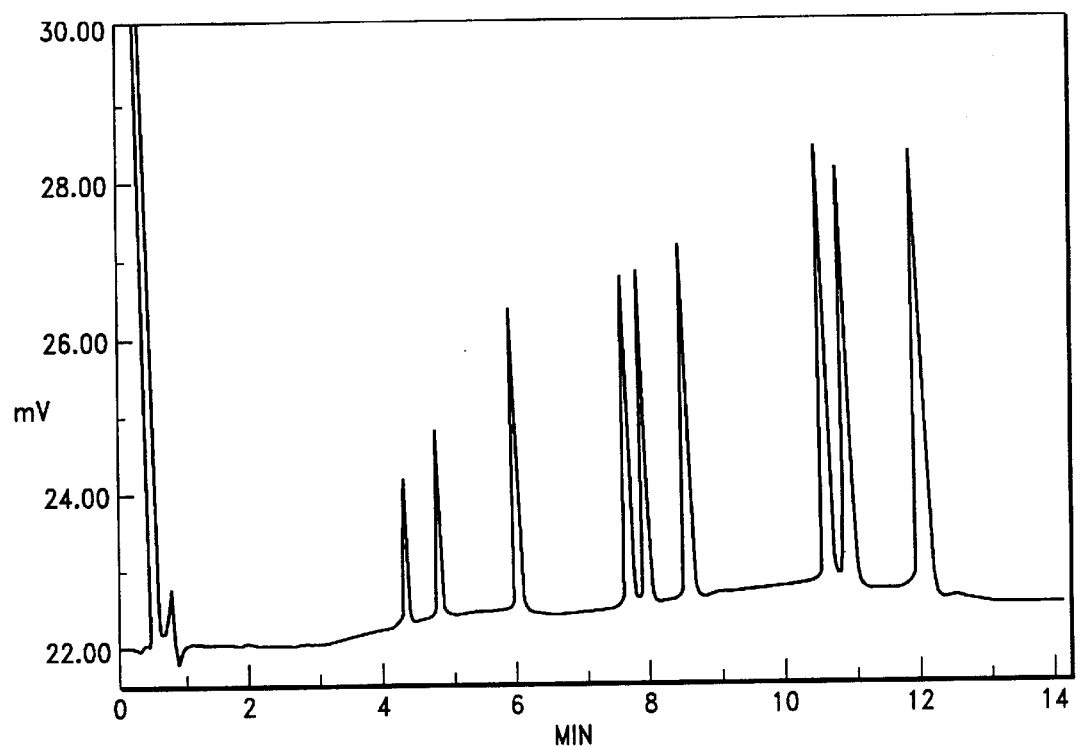
FIG. 17 is a separation using alkylated beads and acetonitrile as solvent.

EXAMPLE 4
Separations With Alkylated and Non-alkylated poly(styrene-divinylbenzene) Beads FIG. 17 shows the high resolution separation of DNA restriction fragments using octadecyl modified, nonporous poly(ethylvinylbenzene-divinylbenzene) beads. The experiment was conducted under the following conditions: Column: 50×4.6 mm i.d.; mobile phase 0.1 M TEAA, pH 7.2; gradient: 33–55% acetonitrile in 3 min, 55–66% acetonitrile in 7 min, 65% acetonitrile for 2.5 min; 65–100% acetonitrile in 1 min; and 100–35% acetonitrile in 1.5 min. The flow rate was 0.75 mL/min, detection UV at 260 nm, column temp. 51° C. The sample was 5 µL (=0.2 µg pUC18 DNA-Hae III digest).

Figure 18:
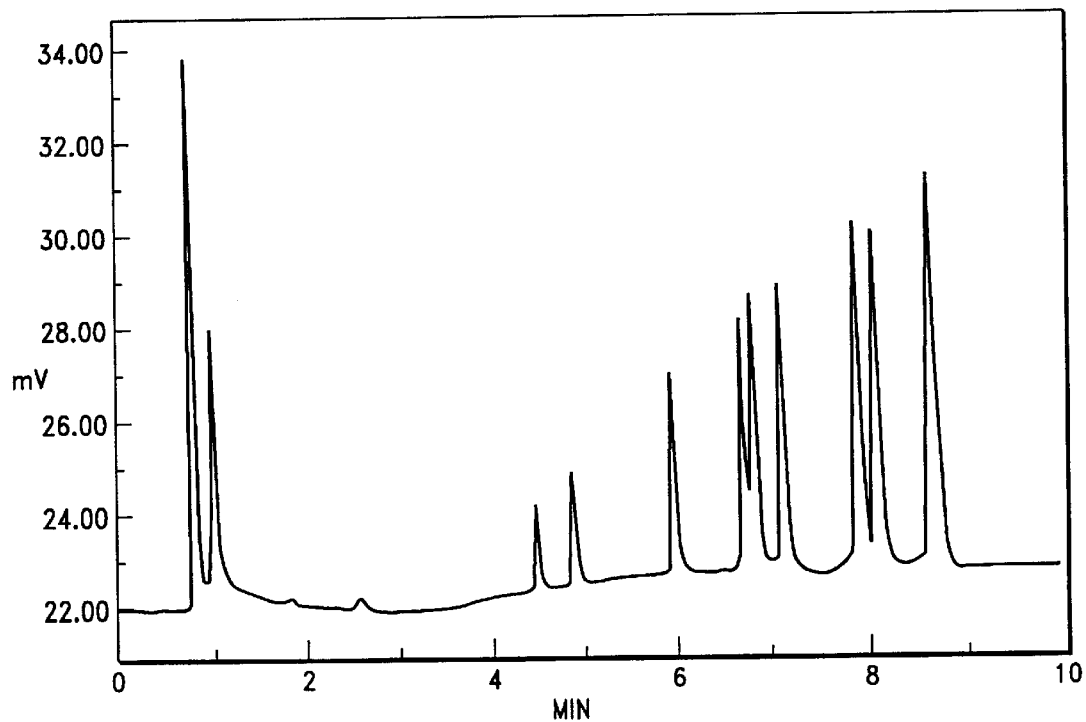
FIG. 18 is a separation using alkylated beads and 50.0% methanol as the solvent.

Repeating the procedure of FIG. 17 replacing the acetonitrile with 50.0% methanol in 0.1 M (TEAA) gave the separation shown in FIG. 18.

Figure 19:
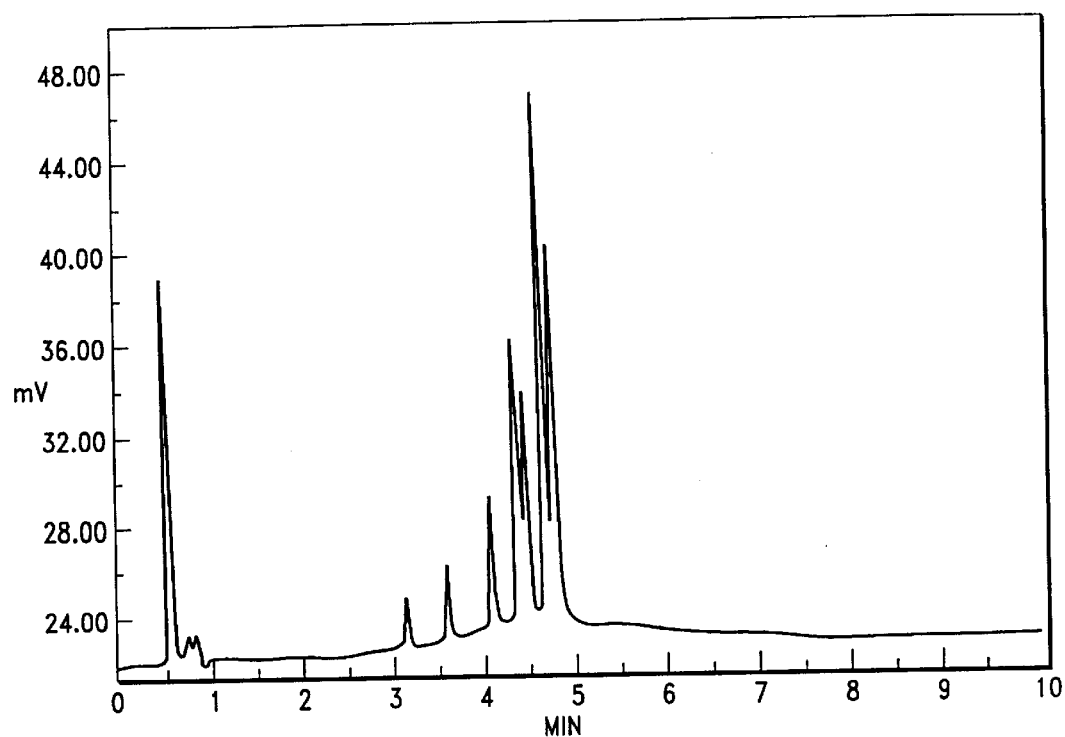
FIG. 19 is a separation using alkylated beads and 25.0% ethanol as the solvent.

Repeating the procedure of FIG. 17 replacing the acetonitrile with 25.0% ethanol in 0.1 M (TEAA) gave the separation shown in FIG. 19.

Figure 20:
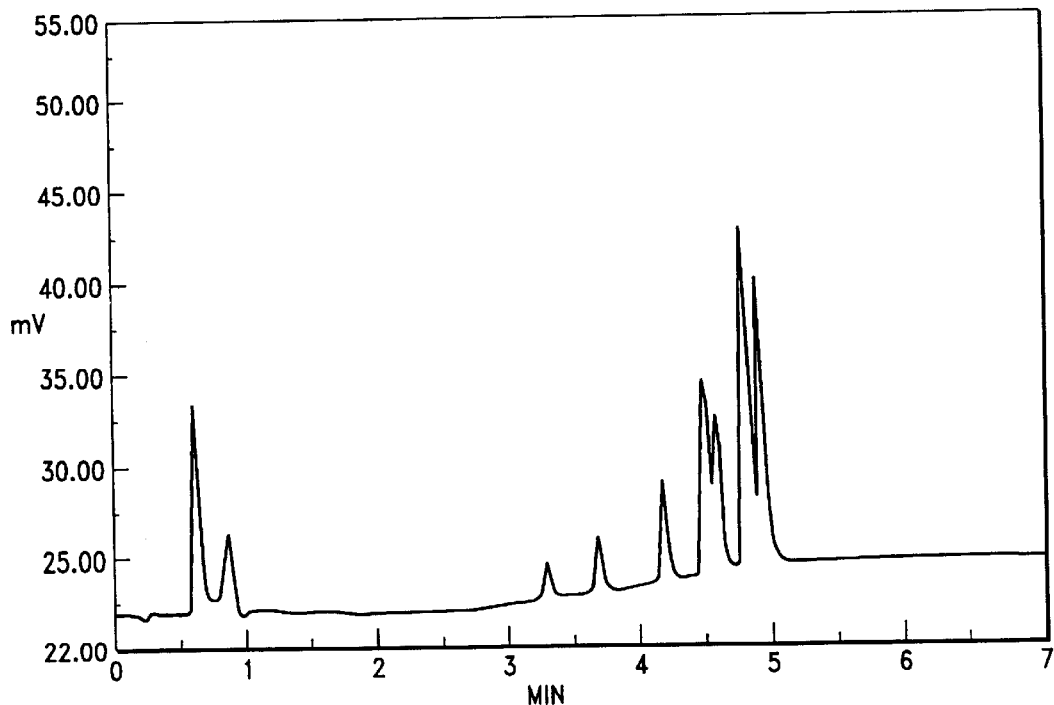
FIG. 20 is a separation using alkylated beads and 25.0% vodka (100 proof) as the solvent.

Repeating the procedure of FIG. 17 replacing the acetonitrile with 25% vodka (Stolichnaya, 100 proof) in 0.1 M (TEAA) gave the separation shown in FIG. 20.

Figure 21:
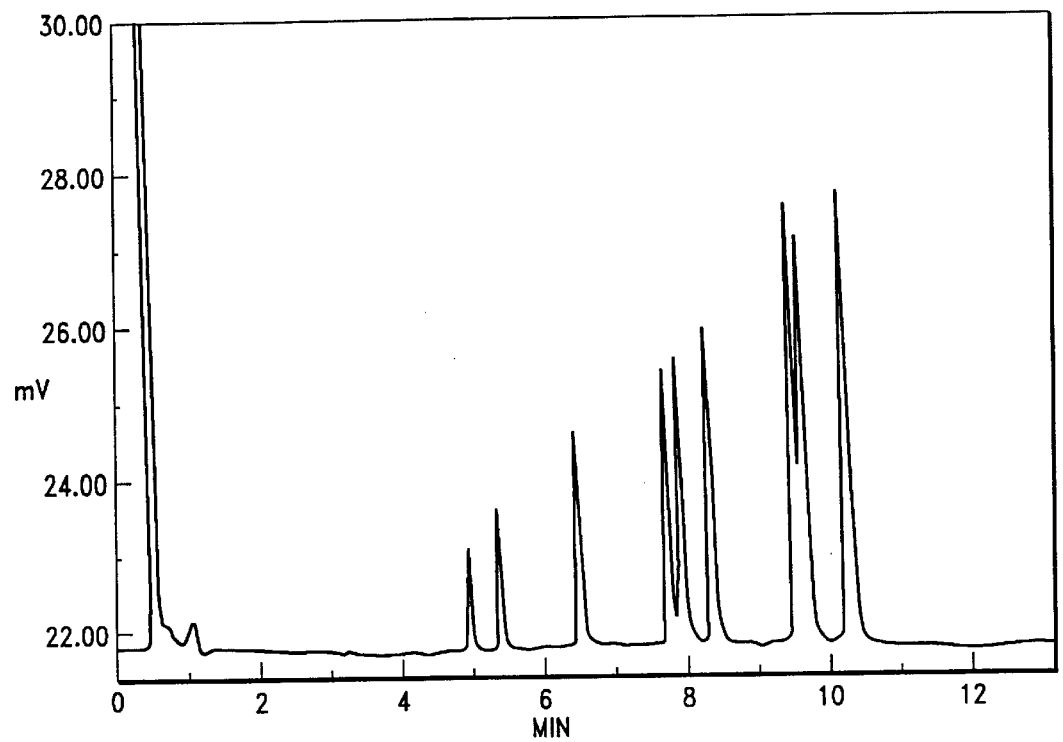
FIG. 21 is a separation using alkylated beads and 25.0% 1-propanol as the solvent.

The separation shown in FIG. 21 was obtained using octadecyl modified, nonporous poly(ethylvinylbenzene-divinylbenzene) beads as follows: Column: 50×4.6 mm i.d.; mobile phase 0.1 M tetraethylacetic acid (TEAA), pH 7.3; gradient: 12–18% 0.1 M TEAA and 25.0% 1-propanol (Eluent B) in 3 min, 18–22% B in 7 min, 22% B for 2.5 min; 22–100% B in 1 min; and 100–12% B in 1.5 min. The flow rate was 0.75 mL/min, detection UV at 260 nm, and column temp. 51° C. The sample was 5 µL (=0.2 1 µg pUC18 DNA-HaeIII digest).

Figure 22:
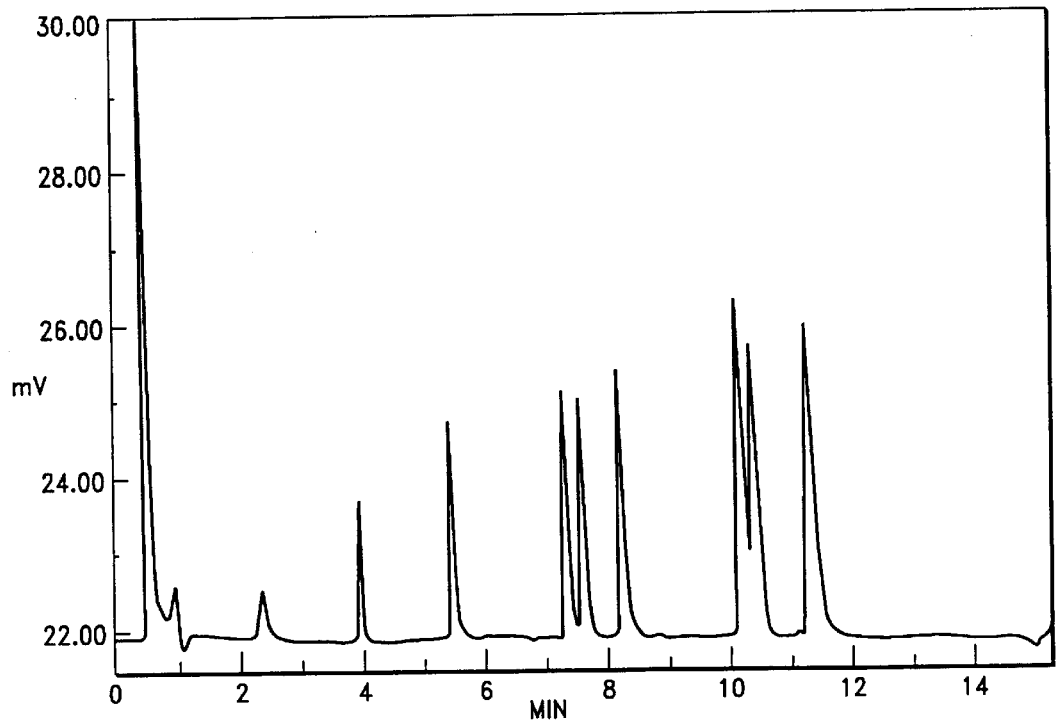
FIG. 22 is a separation using alkylated beads and 25.0% 1-propanol as the solvent.

The separation shown in FIG. 22 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 15–18% 0.1 M TEAA and 25.0% 1-propanol (Eluent B) in 2 min, 18–21% B in 8 min, 21% B for 2.5 min; 21–100% B in 1 min; and 100–15% B in 1.5 min. The flow rate was 0.75 mL/min, detection UV at 260 nm, and column temp. 51° C. The sample was 5 µL (=0.2 µg pUC18 DNA-HaeIII digest).

Figure 23:
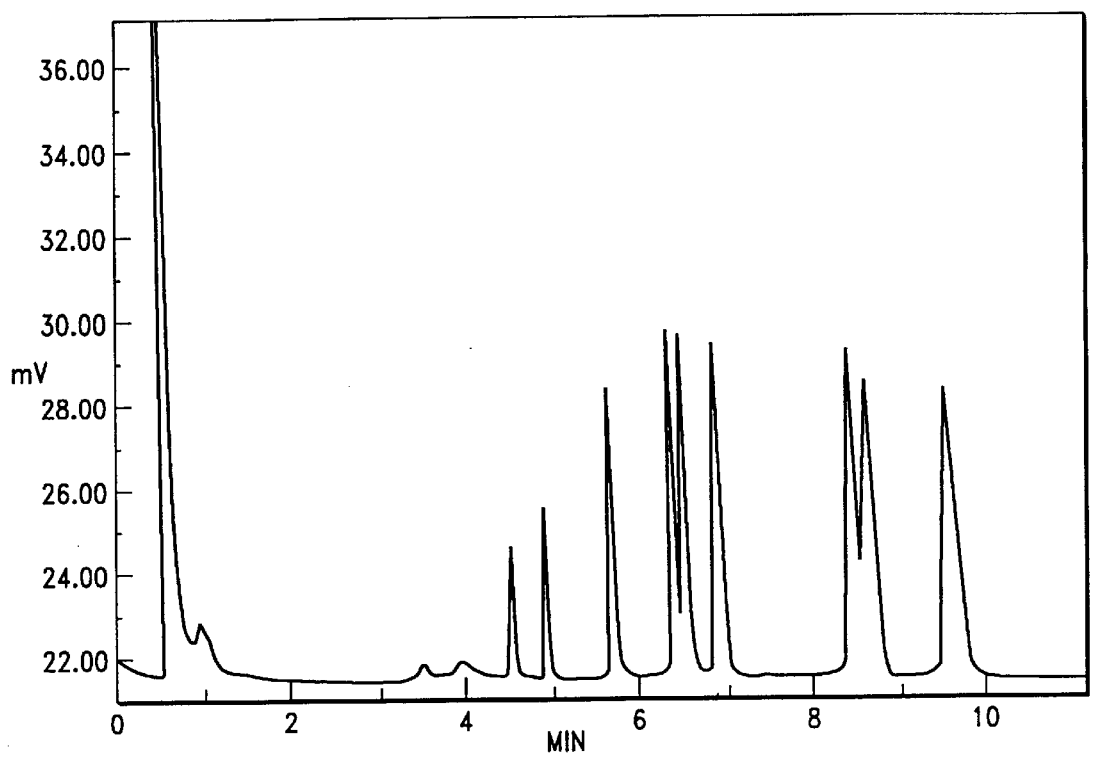
FIG. 23 is a separation using alkylated beads and 10.0% 2-propanol as the solvent.

The separation shown in FIG. 23 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 35–55% 0.1 M TEAA and 10.0% 2-propanol (Eluent B) in 3 min, 55–65% B in 10 min, 65% B for 2.5 min; 65–100% B in 1 min; and 100–35% B in 1.5 min. The flow rate was 0.75 mL/min, detection UV at 260 nm, and column temp. 51° C. The sample was 5 µL (=0.2 µg pUC18 DNA-HaeIII digest).

Figure 24:
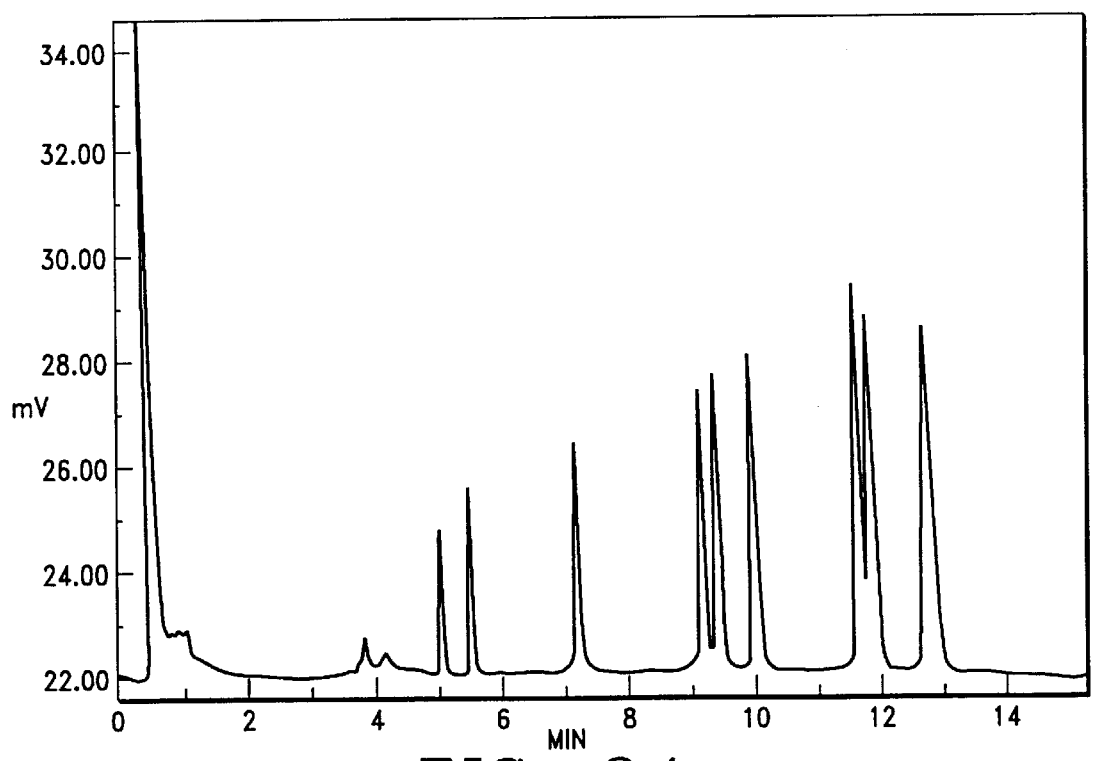
FIG. 24 is a separation using alkylated beads and 10.0% 2-propanol as the solvent.

The separation shown in FIG. 24 was obtained using octadecyl modified, nonporous poly(ethylvinylbenzene-divinylbenzene) beads as follows: Column: 50×4.6 mm i.d.; mobile phase 0.1 M TEA$_2$HPO$_4$, pH 7.3; gradient: 35–55% 0.1 M TEA$_2$HPO$_4$ and 10.0% 2-propanol (Eluent B) in 3 min, 55–65% B in 7 min, 65% B for 2.5 min; 65–100% B in 1 min; and 100–65% B in 1.5 min. The flow rate was 0.75 mL/min, detection UV at 260 nm, and column temp. 51° C. The sample was 5 µL (=0.2 µg pUC18 DNA-HaeIII digest).

Figure 25:
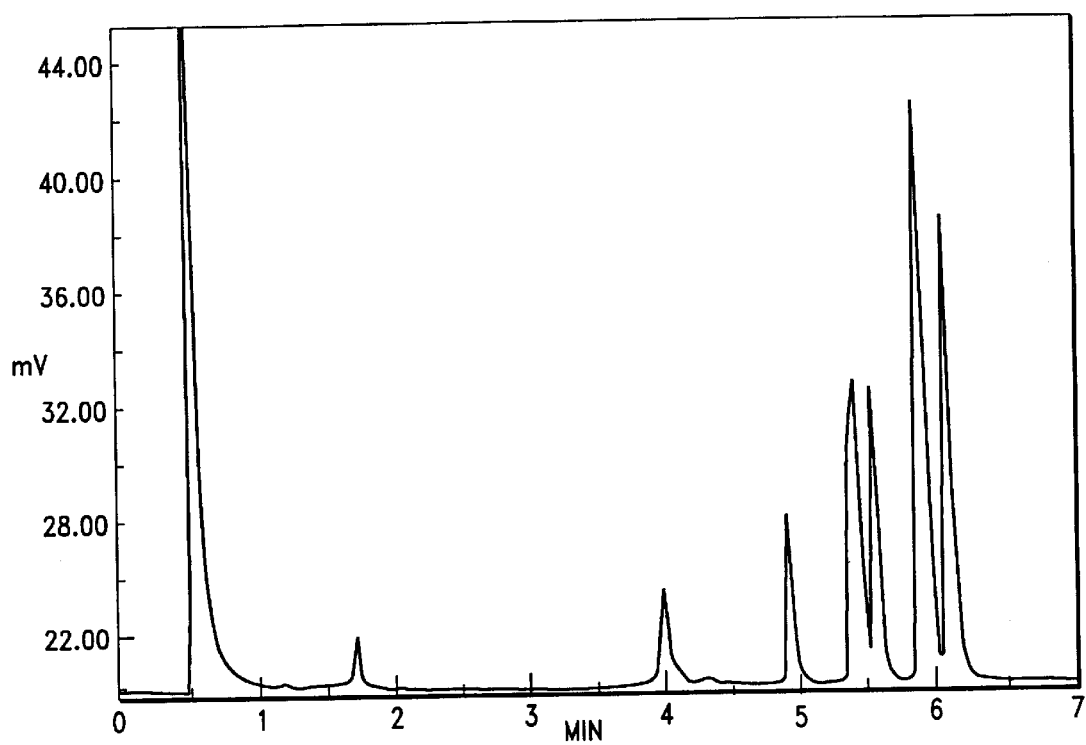
FIG. 25 is a separation using alkylated beads and 25.0% THF as the solvent.

The separation shown in FIG. 25 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 6–9% 0.1 M TEAA and 25.0% THF (Eluent B) in 3 min, 9–11% B in 7 min, 11% B for 2.5 min; 11–100% B in 1 min; and 100–6% B in 1.5 min. The flow rate was 0.75 mL/min, detection UV at 260 nm, and column temp. 51° C. The sample was 5 µL (=0.2 µg pUC18 DNA-HaeIII digest).

EXAMPLE 5
Isocratic/gradient Separation of ds DNA

Figure 26:
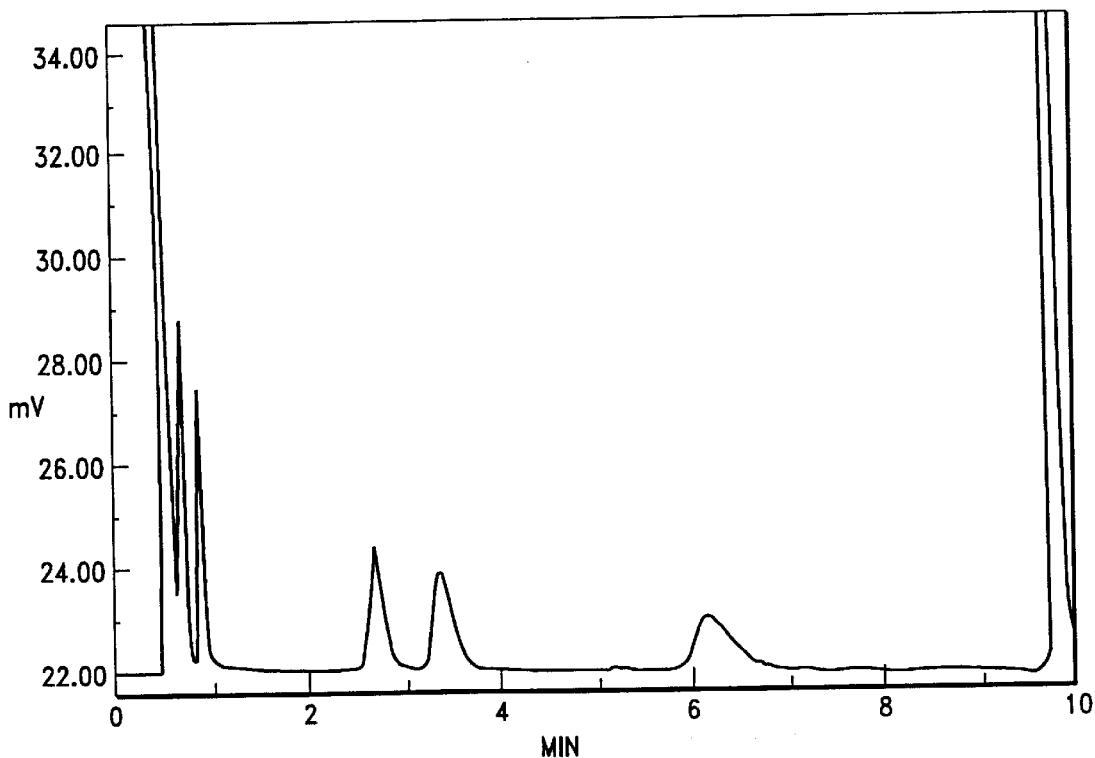
FIG. 26 is an isocratic/gradient separation on non-alkylated poly(styrenedivinylbenzene) beads.

The following is an isocratic/gradient separation of ds DNA using nonporous poly(styrene-divinylbenzene) beads. Isocratic separations have not been performed in DNA separations because of the large differences in the selectivity of DNA/alkylammonium ion pair for beads. However, by using a combination of gradient and isocratic elution conditions, the resolving power of a system can be enhanced for a particular size range of DNA. For example, the range of 250–300 base pairs can be targeted by using an eluent of 0.1 M TEAA, and 14.25% acetonitrile at 0.75 mL/min at 40° C. on 50×4.6 mm cross-linked poly(styrene-divinylbenzene) column, 2.1 micron. 5 µL of pUC18 DNA-HaeIII digest (0.2 µg) was injected under isocratic conditions and 257, 267 and 298 base pairs DNA eluted completely resolved as shown in FIG. 26. Then the column was cleaned from larger fragments with 0.1 M TEAA/25% acetonitrile at 9 minutes. In other examples, there might be an initial isocratic step (to condition the column), then a gradient step (to remove or target the first group of DNA at a particular size), then an isocratic step (to separate the target material of a different size range) and finally a gradient step to clean the column.

EXAMPLE 6
C-18 Bonded Phase Standard Phase

To a 1000-mL round bottomed flask, add 200 g of nonporous, 2 µsilica and one small stirring egg. Transfer flask with silica to an oven and heat at 125° C. overnight (i.e., at least 8 hours). Have heating mantle and condenser set up.

The C-18 bonding reagent, n-octadecyldimethylsilane, is a waxy white solid to semi-solid at room temperature. To transfer, open the bottle in a hood and gently warm with a heat gun (note: pressure can build up in stored chlorosilane bottles, and they should be handled as if they were HCl, as upon contact with moisture, HCl is the side product).

To a second flask, transfer 125 g of the n-octadecylmethylchlorosilane reagent, 10 mL of chloroform, 400 mL of toluene, and 65 mL of pyridine. Mix the liquid reagents by swirling, and then add to the dried silica and swirl until all of the silica is suspended. Attach the refluxing condenser and bring the mixture to reflux for 15 hours. Let the mixture cool, such that refluxing has stopped. Add the capping reagent package of 20 mL of trimethylchlorosilane, 6 mL of hexamethylsilane in 20 mL of toluene. Resuspend the mixture and bring the system back to reflux for 6 hours. Let the mixture cool to room temperature.

Transfer to a Buchner funnel and wash with three 200-mL aliquots of methanol, followed by three 200-mL aliquots of acetone. Air dry for at least 0.5 hour, and then dry in the oven at 100° C. overnight.

Submit sample for elemental analysis, and percent carbon. Dried bonded phase is now ready for column packing.

EXAMPLE 7
CN Bonded Phase, Cyano Phase

To a 1000-mL round-bottomed flask, add 200 g of nonporous, 2 μm silica, one stirring egg, and place in an oven at 125° C. overnight (i.e., at least 8 hours) to dry. To the dried silica, add 100 mL of the 3-cyanopropylmethyldichlorosilane, 10 mL of chloroform, 450 mL of toluene, and 50 mL of pyridine. Suspend the mixture and bring to reflux for 15 hours. Cool filter and wash in a Buchner funnel with one 200-mL aliquot of toluene, followed by two 200-mL aliquots of methanol. Transfer to a beaker and add 300 mL of 50:50 methanol:water, pH 5.5 with HCl. Suspend and let sit at room temperature for 1 hour. Filter onto Buchner funnel and wash phase with methanol and acetone. Transfer to the 1 000-mL round-bottomed flask and dry in oven overnight.

Next, endcap by adding 20 mL of trimethylchlorosilane, 6 mL of hexamethyl-disilane, 350 mL of toluene, 10 mL of chloroform, and 25 mL of pyridine to the dried bonded phase, and bring to reflux for 6 hours. Cool the resulting mixture, transfer to a Buchner funnel, and wash with three 200-mL aliquots of methanol, followed by three 200-mL aliquots of acetone. Air dry for at least 0.5 hour, and then dry in the oven at 100° C. overnight.

Submit a sample for elemental analysis.
The bonded phase is now ready for column packing.

EXAMPLE 8
Dioctyl Silyl Phase—C-8X2

Repeat all of the steps for CN phase, but replace 3-cyanopropylmethyidichlorosilane with 100 mL of dioctyl dichlorosilane.

EXAMPLE 9

The procedures of Example 6 are repeated but the silica is washed with 500 mL of 100 mM HCl and water prior to drying. The product is washed with 500 mL of 100 mM HCl after cooling and prior to the methanol wash.

EXAMPLE 10

The product of Example 6 is coated with 100 mL of dichloromethane containing 1 gram of divinylbenzene and 10 mg of benzoylperoxide. The dichloromethane is removed by rotary evaporation until the monomer is coated onto the beads. While rotating very slowly, the temperature is increased to 70° C. for 8 hours. The product is washed with methanol.

This procedure is repeated with the product of Example 9.

EXAMPLE 11

The procedure of Example 10 is repeated with stearyldivinyl benzene in place of divinylbenzene.

EXAMPLE 12

Fifteen (15) grams of the nonporous silica particles, 50 mL of 2,2,4-trimethylpentane, and 25 mL of vinyltrichlorosilane are refluxed for 2 hours. The modified silica is then washed several times with both 2,2,4-trimethylpentane and acetone and dried at 80° C.

Five (5) grams of the vinyl-coated silica particles prepared as described above are placed in a round bottom flask. Twenty-five mL of acetonitrile containing 2 g of a vinyl monomer (divinylbenzene, styrene, acrylonitrile, acrylic acid, butyl methacrylate, or 2-hydroxy methacrylate) are added and the mixture well dispersed. Twenty-five mL of acetonitrile containing 0.2 g of dibenzoyl peroxide is added, and the mixture is refluxed for 2 hours.

The products are extracted with acetonitrile and then acetone to remove unreacted monomers and oligomers from the particle.

In the case of the acrylic acid-modified silica, extractions with water are also carried out.

The packing materials are dried at 80° C. prior to packing.

EXAMPLE 13

This example demonstrates the high resolution separation of DNA restriction fragments using octadecyl modified, nonporous silica reverse phase material, as described in Example 6. The experiment is conducted under the following conditions: Column: 50×4.6 mm i.d. Mobile phase: 0.1 M TEAA, pH 7.0. Gradient: 8.75–11.25% acetonitrile in 2 minutes, followed by 11.25–14.25% acetonitrile in 10 minutes, 14.5–15.25% acetonitrile in 4 minutes, and by 15.25–16.25% acetonitrile in 4 minutes. Flow rate 1 mL/min. Column temperature: 50° C. Detection: UV at 254 nm. Sample: Mixture of 0.75 μg pBR322 DNA-HaeIII restriction digest and 0.65 μg Φx174 DNA-Hinc II restriction digest.

A high resolution separation is obtained by optimizing the concentration of triethylammonium acetate (TEAA), shape of the gradient curve, column temperature, and flow rate. The resolution of peaks is continuously enhanced in going from 25 mM to at least 125 mM of TEAA. The gradient is optimized by decreasing the steepness of the gradient curve with increasing fragment lengths of DNA molecules. The best separations of double-stranded DNA molecules are accomplished at about 30° C. to 50° C. Denaturation of DNA at higher than about 50° C. prevents utilization of higher column temperatures for double-stranded DNA fragments, although single-stranded DNA separations can be performed at temperatures up to 80° C. and higher.

EXAMPLE 14

If the gradient delay volume is minimized, the separation of PCR products and hybrid polynucleotides derived from various sources of polynucleotides, including living and dead organisms (animal and plant), as well as parts of such organisms (e.g., blood cells, biopsies, sperm, etc.) on octadecyl modified, nonporous poly-(ethylvinylbenzene-divinylbenzene) coated beads can be achieved with run times under 2 minutes.

The analysis of PCR products and hybrid polynucleotides usually requires only separation and detection of one or two species of known length. Because of this, the resolution requirements are considerably less severe than for separations of DNA restriction fragments. Such less stringent resolution requirements allow the utilization of steep gradients and, consequently, lead to still shorter run times. The recovery rate for a DNA fragment containing 404 base pairs is about 97.5%.

Unlike capillary electrophoresis (CE), PCR samples do not have to be desalted prior to analysis by MIPC. This represents a decisive advantage of MIPC over CE. With MIPC, it is thus possible to achieve a fully automated analysis of PCR samples if an automatic autosampler is utilized. Moreover, since the volume of sample injection is known, in contrast to CE, quantitation over several orders of magnitude can be achieved without the need for an internal standard, hence allowing the quantitation of gene expression, as well as the determination of virus titers in tissues and body fluids. A fully automated version of the method of the invention can be used to discriminate (distinguish) normal from mutated genes, as well as to detect oncogenes, bacterial and viral genome polynucleotides (hepatitis C virus, HIV, tuberculosis) for diagnostic purposes. Moreover, adjustment of column temperature allows one to moderate the stringency of hybridization reactions or to separate heteroduplex from homoduplex DNA species.

The suitability of the polymer-coated beads of the invention for clinical use is described under the following conditions: Column: 50×4.6 mm i.d. Mobile phase: 0.1 M TEAA, pH 7.0. Gradient: 11.25–13.75% acetonitrile in 1 minute, followed by 22.5% acetonitrile for 6 seconds, and 11.25% acetonitrile for 54 seconds. Flow rate: 3 mL/min. Column temperature: 50° C. Detection: UV at 256 nm. Sample: 20 µl of a PCR sample. In the separation, the following elution order is obtained: 1=unspecific PCR product, 2=PCR product having 120 base pairs, 3=PCR product having 132 base pairs, and 4=PCR product having 167 base pairs.

PCR methods and processes are described by R. K. Saiki et al. in *Science,* 23):1350–1354 (1985) and K. B. Mullis in U.S. Pat. No. 4,863,202. These references are incorporated herein by reference for a more complete description of methods and processes for obtaining PCR samples which can be separated using the method of the present invention.

The repetitive analysis of PCR products using the method of the invention is highly reproducible under the described analytical conditions. The results are not in any way influenced by the preceding injection. The present method is highly suitable for routine use under real conditions in clinical laboratories.

EXAMPLE 15

The following describes a separation of single-stranded DNA. A silica-C18 column, as described in Example 6, 1.5 micron, 30×4.6 mm i.d., is used with a linear gradient of 2.5–12.5% acetonitrile in 0.1 M triethylammonium acetate in 40 minutes at 1 mL/min and 40° C. A mixture of p(dC)12–18 and p(dT)12–18 oligonucleotides is separated, with the first mixture eluting between 5 and 15 minutes, and the second mixture eluting between 15 and 30 minutes.

EXAMPLE 16
Sorption Enthalpy Measurements

Four fragments (174 base pair, 257 base pair, 267 base pair, and 298 base pair, found in 5 µl pUC18 DNA-HaeIII digest, 0.04 µg DNA/µl) of a DNA digest are separated under isocratical conditions at different temperatures using C-18 alkylated poly(styrene-divinylbenzene) polymer beads. Conditions used for the separation are: Eluent: 0.1 M triethylammonium acetate, 14.25% (v/v) acetonitrile at 0.75 mL/min, detection at 250 nm UV, temperatures at 35, 40, 45, 50, 55, and 60° C., respectively. A plot of ln k versus 1/T (FIG. 14) shows that the retention factor k is increasing with increasing temperature. This indicates that the retention mechanism is based on an endothermic process ($\Delta H_{sorp} > 0$).

The same experiments on non-alkylated poly(styrene-divinylbenzene) beads (FIG. 15) give a negative slope for a plot of ln k versus 1/T, although the plot is slightly curved.

The same experiments on alkylated poly(styrene-divinylbenzene) beads but the acetonitrile solvent is substituted with methanol (FIG. 16) gives a plot ln k versus 1/T shows the retention factor k is decreasing with increasing temperature. This indicates the retention mechanism is based on an exothermic process ($\Delta H_{sorp} < 0$). Replacing the alkylated and non-alkylated polymer beads with silica beads having a coating of alkylated poly(styrene-divinylbenzene) and non-alkylated alkylated poly(styrene-divinylbenzene) will give the same results.

EXAMPLE 17
Isocratic/gradient Separation of dsDNA

The following is an isocratic/gradient separation of dsDNA on a polystyrene coated silica base material. Isocratic separations have not been performed in DNA separations because of the large differences in the selectivity of DNA/alkylammonium ion pair for beads. However, by using a combination of gradient and isocratic elution conditions, the resolving power of a system can be enhanced for a particular size range of DNA. For example, the range of 250–300 base pairs can be targeted by using an eluant of 0.1 M TEAA, and 14.25% acetonitrile at 0.75 mL/min at 40° C. on 50×4.6 mm crosslinked polystyrene coated silica reverse phase column, 2.0 micron. The pUC18 DNA-HaeIII digest was injected under isocratic conditions and 257, 267 and 298 base pairs DNA eluted completely resolved. Then the column was cleaned from larger fragments with 0.1M TEAA/ 25% acetonitrile at 9 minutes. FIG. 17 shows a separation using the same elution conditions but performed on a poly(styrene-divinylbenzene) polymer based column. In other examples, there might be an initial isocratic step (to condition the column), then a gradient step (to remove or target the first group of DNA at a particular size), then an isocratic step (to separate the target material of a different size range) and finally a gradient step to clean the column.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

While various embodiments and features of the invention have been described, those skilled in the art will recognize that variations and additions to those features and functions can be made within the scope of the invention. The invention is therefore intended to be limited only by the scope of the appended claims.

We claim:

1. A method for producing an array of bands, each band representing a specific fraction of double stranded DNA having a calculated base-pair length, comprising the steps of
   a) separating a mixture of double stranded nucleic acid fragments into base-pair length fractions by reversed phase ion pairing chromatography, wherein the separated base pair length fractions are eluted from a chromatography column;
   b) detecting the separated base-pair length fractions as they elute from the column;
   c) providing a digitized signal corresponding to the detected base-pair length fractions; and
   d) displaying the digitized signal as an array of bands, each band corresponding to a base-pair length fraction.

2. The method of claim 1 including calculating the base-pair length of each of the fractions, and displaying the base-pair length of each fraction in association with the respective band.

3. The method of claim 1 wherein the separated base-pair length fractions are detected by a UV detector, fluorescence detector or radioactivity detector.

4. The method of claim 1 wherein the position of a band in the array of bands correlates to the number of base pairs of the DNA in a respective fraction.

5. The method of claim 1 wherein the array of bands is displayed as an array of lines or rectangles.

6. The method of claim 1 wherein each of the bands is displayed in color, and the color in each band correlates to the amount of fragments represented in each band.

7. The method of claim 1 wherein each of the bands is displayed in a gray scale, and the level of the gray scale of each band correlates to the amount of fragments represented in each band.

8. An apparatus for producing an array of bands, each band representing a specific fraction of double stranded DNA having a calculated base-pair length, comprising:
   a) a reversed phase ion pairing chromatography system for separating a mixture of double stranded nucleic acid fragments into base-pair length fractions, wherein the chromatography system includes chromatography column with an outlet at one end from which the separated base-pair length fractions are eluted;
   b) a detector positioned at the output of the column to detect the separated base-pair length fractions as they elute off the column; and
   c) a computer and software to provide a digitized signal corresponding to the detected base-pair length fractions and to display the digitized signal as an array of bands, each band corresponding to a base-pair length fraction.

9. The apparatus of claim 8 wherein the computer and software calculate the base-pair lengths of each of the fractions.

10. The apparatus of claim 9 wherein the computer and software display the base-pair length of each fraction in association with the respective band.

11. The apparatus of claim 8 wherein the fractions are detected by a UV detector, fluorescence detector or radioactivity detector.

12. The apparatus of claim 8 wherein the computer and software display the array of bands so that the position of a band in the array of bands correlates to the base-pair length of a respective fraction.

13. The apparatus of claim 8 wherein the computer and software display the bands as an array of lines or rectangles.

14. The apparatus of claim 8 wherein the computer and software display the bands in color, and the color in each band correlates to the amount of fragments represented in each band.

15. The apparatus of claim 8 wherein the computer and software display the bands in a gray scale, and the level of the gray scale of each band correlates to the amount of fragments represented in each band.

16. The apparatus of claim 8 wherein the computer and software calculate the base-pair lengths of the DNA in each fraction, the concentration of DNA in each fraction, and the separation time of each fraction for each band in the array of bands.

* * * * *